United States Patent
Abdul-Rahman

(10) Patent No.: US 6,967,205 B1
(45) Date of Patent: Nov. 22, 2005

(54) COMPOUNDS WITH ANTIBACTERIAL AND ANTIPARASITIC PROPERTIES

(75) Inventor: Shoaá Abdul-Rahman, Lund (SE)

(73) Assignee: New Pharma Research Sweden AB, Lund (SE)

(*) Notice: Subject to any disclaimer, the term of this patent is extended or adjusted under 35 U.S.C. 154(b) by 368 days.

(21) Appl. No.: 10/111,898

(22) PCT Filed: Nov. 13, 2000

(86) PCT No.: PCT/SE00/02217

§ 371 (c)(1),
(2), (4) Date: May 15, 2002

(87) PCT Pub. No.: WO01/36408

PCT Pub. Date: May 25, 2001

(30) Foreign Application Priority Data

Nov. 15, 1999 (SE) .................................... 9904108

(51) Int. Cl.⁷ ............................................... A61K 31/44
(52) U.S. Cl. ....................... 514/291; 514/292; 514/293; 546/82; 546/173; 546/268; 546/281.7
(58) Field of Search .......................... 546/156; 514/312

(56) References Cited

U.S. PATENT DOCUMENTS

| 5,164,402 A | 11/1992 | Brighty |
| 5,225,413 A | 7/1993 | Naik et al. |
| 5,266,569 A | 11/1993 | Brighty |

FOREIGN PATENT DOCUMENTS

| DE | 3608745 | 9/1981 |
| DE | 3632222 | 4/1988 |
| DE | 3637649 | 4/1988 |
| EP | 0047005 | 3/1982 |
| EP | 0049355 | 4/1982 |
| EP | 0078362 | 5/1983 |
| EP | 0140116 | 5/1985 |
| EP | 0154780 | 9/1985 |
| EP | 0165375 | 12/1985 |
| EP | 0131839 | 1/1986 |
| EP | 0268223 | 5/1988 |
| EP | 0354453 | 2/1990 |
| EP | 0676199 | 10/1995 |
| GB | 2057440 | 4/1981 |
| GB | 1598915 | 9/1981 |
| GB | 2093018 | 8/1982 |
| WO | 9638417 | 12/1996 |

OTHER PUBLICATIONS

Antimicrobial Agents and Chemotherapy, vol. 43, No. 8, Aug. 1999. Elizabeth Nenortas et al., "Antitrypanosomal Activity of Fluoroquinolones" p. 2066–p. 2068.

Primary Examiner—James O. Wilson
Assistant Examiner—Jason H. Johnsen
(74) Attorney, Agent, or Firm—Burns, Doane, Swecker & Mathis, LLP

(57) ABSTRACT

There are provided novel compounds which have both antibacterial and antiparasitic properties, thereby reducing the need for using several compounds in combined antibacterial and antiparasitic treatment of livestock. The present novel compounds are especially well suited for treatment of coccidiosis, and they are represented by general formula (I) wherein $R_1$–$R_6$, X and A are as defined in the specification.

9 Claims, No Drawings

COMPOUNDS WITH ANTIBACTERIAL AND ANTIPARASITIC PROPERTIES

FIELD OF THE INVENTION

The present invention relates to novel compounds, pharmaceutical compositions containing the same as well as a method for treatment of bacterial and parasitic disorders, wherein said compounds are administered.

BACKGROUND OF THE INVENTION

The *coccidia* are intracellular protozoan parasites which are prevalent in all domestic animals as well as in man. They are the cause of coccidiosis, which is characterized by enteritis. *Coccidia* of the genus *Eimeria* cause severe intestinal infections in poultry and ruminants (cattle, sheep e.t.c.). In fact, coccidiosis is one of the most frequently occurring diseases of poultry (see inter alia "Poultry Diseases" by Jordan, F. T. W. and Pattison, M., 4$^{th}$ ed., pp. 261–276, 1996, W. B. Saunders Co. Ltd., London, UK). It deserves mentioning that the annual costs for anticoccidial medication is about £5 million in the UK only. In poultry, most cases of coccidiosis are caused by protozoa belonging to the genus *Eimeria*, such as e.g. *E. maxima, E. tenella, E. acervulina, E. necatrix, E. hagani, E. praecox, E. mitis* and *E. brunetti*. Other examples of infectious *Eimeria* protozoa are *E. gallopavonis, E. meleagrimitis, E. adenoeides, E. meleagridis, E. dispersa, E. innocua, E. subrotunda, E. truncata, E. anseris, E. bovis, E. zurnii, E. alabamansis, E. auburnensis, E. ashsata, E. parva, E. faurei, E. arloingi, E. debliecki* and *E. spinosa*.

In poultry, e.g. chickens and turkeys, an outbreak of coccidiosis may with little or no forewarning lead to a serious infection, and unless the birds are promptly treated, the result may be a very high mortality. Animals that survive these types of infections are usually of reduced economical value, since they become less efficient in converting feed to weight gain, grow much more slowly than normal animals and frequently appear listless. A similar disease scenario may also occur upon *coccidia* infection of larger animals, e.g. ruminants and pigs, albeit the problem is in general more severe in poultry.

In the treatment of coccidiosis, a recognized problem is the development of resistance to known anticoccidial agents. This problem has been addressed in numerous publications, such as in Stephen B. et al., *Vet. Parasitol.*, 69(1–2), pp 19–29, 1997.

Thus, there is a general need in the art for both new and improved antiparasitic compounds, particularly for the treatment of coccidiosis.

Furthermore, antibacterial agents such as enrofloxacin (U.S. Pat. No. 4,670,444) are often added to animal feed, and this often leads to resistance problems. Indeed, new antibacterial compounds is an ongoing need in the art.

Moreover, there is a general public demand to reduce the number of added drugs in animal feed.

DISCLOSURE OF THE INVENTION

There are now provided novel compounds which surprisingly have both antibacterial and antiparasitic properties, thereby reducing the need for using several prior art compounds in e.g. combined antibacterial and antiparasitic treatment of livestock. Furthermore, the present novel compounds are especially well suited for treatment of coccidiosis (vide infra). More specifically, the present invention relates to a compound having the general formula (I):

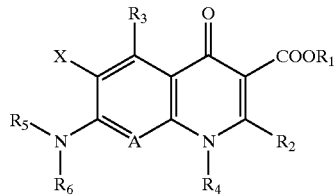

(I)

wherein
X is selected from F, Cl, I, CN, SH, $NO_2$, $CF_3$, $COOR_1$, $CONR_7R_8$, NH-aryl, $NHSO_2R_{15}$ and $(CH_2)_{1-5}NHSO_2R_{15}$, wherein $R_1$, $R_7$, $R_8$, $R_{15}$ and aryl are as defined hereinbelow;
$R_2$–$R_3$ are independently selected from a group of substituents (a)–(h) consisting of
  (a) H;
  (b) straight chain, branched or cyclic saturated or unsaturated alkyl, mono-, di- or trifluoroalkyl, hydroxyalkyl or alkoxyalkyl having 1–6 carbon atoms;
  (c) (O-alkyl)$_z$, (alkyl-O)$_z$-alkyl, (S-alkyl)$_z$, (alkyl-S)$_z$-alkyl, (alkyl-S—S)$_z$-alkyl, N-(alkyl)$_n$, alkyl-N-(alkyl)$_n$, alkyl-NH$_2$, alkyl-NHSO$_2$-alkyl or alkyl-NHSO$_2$-aryl, where alkyl is as defined in (b) and optionally contains at least one substituent X, aryl is as defined in (e), z is an integer from 1 to 5 and n is 1 or 2;
  (d) (C(O)-alkyl)$_z$, (O—C(O)-alkyl)$_z$, (S—C(O)-alkyl)$_z$ or (NH—C(O)-alkyl)$_z$, where alkyl is as defined in (b) and z as defined in (c);
  (e) aryl, condensed aryl or aralkyl, optionally containing at least one heteroatom selected from N, S and O and/or at least one substituent selected from X and (a)–(d);
  (f) O-aryl, C(O)-aryl, C(O)-heteroaryl, O-aralkyl, N-(aryl)$_n$, N-(aralkyl)$_n$ or N—(SO$_2$-aryl)$_n$, where aryl is as defined in (e) and n is 1 or 2;
  (g) X;
  (h) NR$_7$R$_8$, wherein R$_7$ and R$_8$ independently are selected from the substituents (a)–(f), wherein NR$_7$R$_8$ optionally may form a five- or six-membered saturated or unsaturated ring;
R$_1$ is selected from the substituents (a)–(b);
A is a radical selected from —N— and —CR$_9$—, wherein R$_9$ is selected from the substituents (a)–(h) or is a C—Y bond to a radical —YCR$_{10}$R$_{11}$CR$_{12}$R$_{13}$—, wherein R$_{10}$–R$_{13}$ are independently selected from the substituents (a)–(h) and Y is selected from S, O and NR$_{14}$,
wherein R$_{14}$ is selected from the substituents (a)–(h)
R$_4$ is selected from the substituents (a)–(h) or may optionally be a C—C bond to said radical —YCR$_{10}$R$_{11}$CR$_{12}$R$_{13}$—;
R$_5$ and R$_6$ are either independently selected from the substituents (a)–(h) and a group of substituents (i)–(m) consisting of
  (i) furanyl, furyl, pyranyl, piperidinyl, morpholinyl, pyridinyl, pyrazinyl, piperazinyl and pyrrolidinyl, optionally containing at least one substituent selected from X and (a)–(d);
  (j) alkylfuranyl, -furyl, -pyranyl, -piperidinyl, -morpholinyl, -pyridinyl, -pyrazinyl, -piperazinyl, and -pyrrolidinyl, optionally containing at least one substituent selected from X and (a)–(d);
  (k) SO$_2$R$_{15}$, where R$_{15}$ is selected from the substituents (a)–(f) and (h)–(j);
  (l) C(S)—NR$_{16}$R$_{17}$ or C(O)—NR$_{16}$R$_{17}$, where R$_{16}$–R$_{17}$ are independently selected from the substituents (a)–(k);

(m) cycloalkyl-$NR_{16}R_{17}$, alkylcycloalkyl-$NR_{16}R_{17}$, cycloalkyl-X or alkylcycloalkyl-X, where $R_{16}$ and $R_{17}$ are as defined in (l) and the cycloalkyl moiety has 3–7 carbon atoms;

with the proviso that at least one of $R_5$ and $R_6$ is selected from the substituents (c)–(m) and that $R_4$ is selected from saturated cycloalkyl and aryl, optionally containing at least one heteroatom selected from N, S and O and/or at least one substituent selected from X and (a)–(d);

or taken together with the nitrogen atom to which they are attached form a group selected from (n)–(p) consisting of (n) structure showing piperazine ring with N—, $R_{18}$, $R_{19}$, N—$R_{22}$, $R_{20}$, $R_{21}$ wherein
$R_{18}$–$R_{21}$ are independently selected from the substituents (a)–(b);
$R_{22}$ is selected from the substituents (c)–(m);

(o) structure showing N—$(CH_2)_{1-3}$ with $R_{23}$, $R_{24}$, $R_{25}$, $R_{26}$ wherein
$R_{23}$ and $R_{25}$ are independently selected from the substituents (a)–(f) or may optionally be part of a C=N bond;
$R_{24}$ and $R_{26}$ are independently selected from the group of substituents (a)–(m) and a group of substituents (q)–(s) consisting of (q) alkyl-$NR_{27}R_{28}$, where $R_{27}$–$R_{28}$ are independently selected from the substituents (a)–(m);
(r) $NR_{27}R_{20}$, where $R_{23}$–$R_{28}$ are as defined in (q);
(s) a =N=O-alkyl radical;

with the proviso that $R_{23}$–$R_{25}$ are not all H when $R_{26}$ is $NH_2$, X is F, A is —CCl—; $R_1$–$R_3$ are H and $R_4$ is cyclopropyl;
with the proviso that at least one of $R_{27}$ and $R_{28}$ in (q) is selected from the substituents (c)–(m) when X is F, A is —$COCH_3$— or —N—, $R_1$–$R_3$ are H and $R_4$ is cyclopropyl;

(p) bicyclic structure with N—, H, H, $NR_{27}R_{28}$ wherein
$R_{27}$–$R_{28}$ are as defined in (q), with the proviso that at least one of $R_{27}$ and $R_{28}$ is selected from the substituents (c)–(m);
tautomers, solvates and radiolabelled derivatives thereof; and
pharmaceutically acceptable salts thereof.

As examples of pharmaceutically acceptable salts mention can be made of acid addition salts, e.g. a salt formed by reaction with hydrohalogen acids, such as hydrochloric acid, sulphuric acid, phosphoric acid, nitric acid, aliphatic, alicyclic, aromatic or hetero-cyclic sulphonic or carboxylic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulphonic acid, ethanesulphonic acid, hydroxyethanesulphonic acid, halogenbensensulphonic acid, toluenesulphonic acid and naphtalenesulphonic acid.

In preferred embodiments of the present invention, $R_1$ is H. Moreover, X is preferably F.

In one of the most preferred embodiments, a compound according to the present invention has the general formula (II):

(II) quinolone structure with $R_3$, O, H, $R_{19}$, F, COOH, $R_{22}$—N, N, H, $R_{21}$, $R_9$, $R_4$ wherein $R_3$, $R_4$, $R_9$, $R_{19}$, $R_{21}$ and $R_{22}$ are as previously defined.

Preferably, $R_3$ is selected from a group of substituents consisting of H, $CH_3$, $NH_2$, (6-chloro-2-pyridinyl)amino, (6-chloro-2-pyrazinyl)amino, (4-fluorophenyl) sulfonyllamino and [(4-nitrophenyl)sulfonyl]amino.

Preferably, $R_4$ is selected from a group of substituents consisting of cyclopropyl, ethyl, 2-fluoroethyl, 4-fluorophenyl and 2,4-difluorophenyl.

Preferably, $R_9$ is either H or F.

Preferably, $R_{19}$ and $R_{21}$ are independently either H or $CH_3$.

Preferably, $R_{22}$ is selected from a group of substituents consisting of (4-nitroanilino)carbothioyl, anilinocarbothioyl, (4-fluoroanilino)carbothioyl, {4-nitro[(4-nitrophenyl)sulfonyl]anilino}carbothioyl, (4-nitroanilino)carbonyl, (4-fluoroanilino)carbonyl, (4-nitrophenyl)sulfonyl, 6-chloro-2-pyridinyl, 6-chloro-2-pyrazinyl, phenylsulfonyl, (4-methylphenyl)sulfonyl, (4-methoxyphenyl)sulfonyl, 2-naphthylsulfonyl, mesitylsulfonyl, propylsulfonyl, benzylsulfonyl, methylsulfonyl, (trifluoromethyl)sulfonyl, (5-bromo-2-thienyl)sulfonyl, (3,5-dichloro-2-hydroxyphenyl)sulfonyl, 5-bromo-2-pyridinyl, 3-chloro-2-sulfanylphenyl, (5-chloro-2-thienyl)sulfonyl, 2-pyrazinyl, {4-fluoro[(4-fluorophenyl)sulfonyl]anilino}carbothioyl, {4-fluoro[(4-nitrophenyl)sulfonyl]anilino}carbothioyl, [(6-chloro-2-pyrazinyl)-4-fluoroanilino]carbothioyl, [(6-chloro-2-pyridinyl)-4-fluoroanilino]carbothioyl, (4-fluorophenyl)sulfonyl, 6-{[(4-fluorophenyl)sulfonyl]amino}-2-pyridinyl, 4-pyridinylmethyl, 4-carboxycyclohexyl, 4-carboxybenzyl, tetrahydro-2-furanylmethyl, 4-isopropylphenyl, 2-(1-piperidinyl)ethyl, 2-[(2-{[(4-fluorophenyl)sulfonyl]amino}ethyl)disulfanyl]ethyl, 2-[(2-{[(4-nitrophenyl)sulfonyl]amino}ethyl)disulfanyl]ethyl, 2-[2-({[(4-nitrophenyl)sulfonyl]amino}methoxy)ethoxy]ethyl, 2-(2-{[(6-chloro-2-pyrazinyl)amino]methoxy}ethoxy)ethyl, 2-(1-pyrrolidinyl)ethyl, (4-nitroanilino)carbothioyl, [3-({[(4-fluorophenyl)sulfonyl]amino}methyl)cyclohexyl]methyl, 3-[(3-aminopropyl)(methyl)amino]propyl, 3-aminopropyl, 3-{[(trifluoromethyl)sulfonyl]amino}propyl, 3-{[(4-nitrophenyl)sulfonyl]amino}propyl, 3-(dimethylamino)-2,2-dimethylpropyl, 2-thienylcarboyl, 2-aminocyclohexyl, 2-{[(trifluoromethyl)sulfonyl]amino}ethyl, 2-{[(4-nitrophenyl)sulfonyl]amino}ethyl, 2,2-dimethyl-3-{[(trifluoromethyl)

sulfonyl]amino}propyl, phenethylsulfonyl, acetoacetyl, 2-(4-pyridinyl)ethyl, 2-(2-pyridinyl)ethyl and 2-methoxy-1-methylethyl.

Most preferably, a compound according to the formula (II) is selected from the compounds disclosed in the following Table 1, the systematic names of which are also given hereinbelow:

TABLE 1

| $R_3$ | $R_4$ | $R_9$ | $R_{19}$ | $R_{21}$ | $R_{22}$ | Denoted |
|---|---|---|---|---|---|---|
| H | 4-fluoro-phenyl | H | H | H | (4-nitro-anilino)-carbothioyl | B626 |
| H | 2-fluoro-ethyl | F | H | H | (4-nitro-anilino)-carbothioyl | B628 |
| $CH_3$ | cyclo-propyl | H | $CH_3$ | H | (4-nitro-anilino)-carbothioyl | B629 |
| H | ethyl | F | $CH_3$ | H | (4-nitro-anilino)-carbothioyl | B630 |
| $NH_2$ | cyclo-propyl | F | H | H | (4-nitro-anilino)-carbothioyl | B633 |
| H | 2,4-di-fluoro-phenyl | H | $CH_3$ | H | (4-nitro-anilino)-carbothioyl | B634 |
| H | 2,4-di-fluoro-phenyl | H | $CH_3$ | H | {4-nitro[(4-nitrophenyl)sulfonyl]-anilino}-carbothioyl | B635 |
| H | ethyl | F | $CH_3$ | H | anilino-carbothioyl | B636 |
| H | cyclo-propyl | H | H | H | (4-fluoro-anilino)-carbothioyl | B637 |
| H | ethyl | H | H | H | (4-nitro-anilino)-carbothioyl | B638 |
| H | cyclo-propyl | H | H | H | (4-nitro-anilino)-carbonyl | B700 |
| H | ethyl | F | $CH_3$ | H | (4-nitro-anilino)-carbonyl | B702 |
| H | 4-fluoro-phenyl | H | H | H | (4-nitro-phenyl)-sulfonyl | JAP 203 |
| H | 4-fluoro-phenyl | H | H | H | 6-chloro-2-pyridinyl | JAP 204 |
| H | 4-fluoro-phenyl | H | H | H | 6-chloro-2-pyrazinyl | JAP 205 |
| H | 2-fluoro-ethyl | F | H | H | (4-nitro-phenyl)-sulfonyl | JAP 206 |
| H | 2-fluoro-ethyl | F | H | H | 6-chloro-2-pyridinyl | JAP 207 |
| H | 2-fluoro-ethyl | F | H | H | 6-chloro-2-pyrazinyl | JAP 208 |
| $CH_3$ | cyclo-propyl | H | $CH_3$ | H | (4-nitro-phenyl)-sulfonyl | JAP 209 |
| $CH_3$ | cyclo-propyl | H | $CH_3$ | H | 6-chloro-2-pyridinyl | JAP 210 |
| $CH_3$ | cyclo-propyl | H | $CH_3$ | H | 6-chloro-2-pyrazinyl | JAP 211 |
| H | ethyl | F | $CH_3$ | H | (4-nitro-phenyl)-sulfonyl | JAP 213 |
| H | ethyl | F | $CH_3$ | H | 6-chloro-2-pyridinyl | JAP 214 |
| [(4-nitro-phenyl)sulphonyl]amino | cyclo-propyl | F | H | H | (4-nitro-phenyl)-sulfonyl | JAP 221 |
| [(4-nitro-phenyl)sulphonyl]amino | cyclo-propyl | F | $CH_3$ | $CH_3$ | (4-nitro-phenyl)-sulphonyl | JAP 222 |
| (6-chloro-2-pyridinyl)-amino | cyclo-propyl | F | $CH_3$ | $CH_3$ | 5-chloro-2-pyridinyl | JAP 223 |
| (6-chloro-2-pyrazinyl)-amino | cyclo-propyl | F | $CH_3$ | $CH_3$ | 6-chloro-2-pyrazinyl | JAP 224 |
| H | 2,4-difluoro-phenyl | H | $CH_3$ | H | (4-nitro-phenyl)-sulfonyl | JAP 225 |
| H | 2,4-difluoro-phenyl | H | $CH_3$ | H | 6-chloro-2-pyrazinyl | JAP 226 |
| H | 2,4-difluoro-phenyl | H | $CH_3$ | H | 6-chloro-2-pyridinyl | JAP 227 |
| H | cyclo-propyl | H | H | H | phenyl-sulfonyl | JA 1 |
| H | cyclo-propyl | H | H | H | (4-methyl-phenyl)-sulfonyl | JA 2 |
| H | cyclo-propyl | H | H | H | (4-nitro-phenyl)-sulfonyl | JA 3 |
| H | cyclo-propyl | H | H | H | (4-methoxy-phenyl)-sulfonyl | JA 4 |
| H | cyclo-propyl | H | H | H | 2-naphthyl-sulfonyl | JA 5 |
| H | cyclo-propyl | H | H | H | mesityl-sulfonyl | JA 6 |
| H | cyclo-propyl | H | H | H | propyl-sulfonyl | JA 7 |
| H | cyclo-propyl | H | H | H | benzyl-sulfonyl | JA 9 |
| H | cyclo-propyl | H | H | H | methyl-sulfonyl | JA 10 |
| H | cyclo-propyl | H | H | H | (trifluoromethyl)-sulfonyl | JA 12 |
| H | cyclo-propyl | H | H | H | (5-bromo-2-thienyl)-sulfonyl | JA 13 |
| H | cyclo-propyl | H | H | H | (3,5-di-chloro-2-hydroxy-phenyl)-sulfonyl | JA 14 |
| H | ethyl | H | H | H | (4-nitro-phenyl)-sulfonyl | JA 20 |
| H | ethyl | H | H | H | (4-methoxy-phenyl)-sulfonyl | JA 21 |
| H | ethyl | H | H | H | benzyl-sulfonyl | JA 26 |
| H | ethyl | H | H | H | (3,5-dichloro-2-hydroxy-phenyl)-sulfonyl | JA 31 |
| H | cyclo-propyl | H | H | H | 6-chloro-2-pyrazinyl | JA 39 |
| H | cyclo-propyl | H | H | H | 5-bromo-2-pyridinyl | JA 40 |
| H | cyclo-propyl | H | H | H | 3-chloro-2-sulfanyl-phenyl | JA 41 |
| H | cyclo-propyl | H | H | H | 6-chloro-2-pyridinyl | JA 42 |
| H | cyclo-propyl | H | H | H | (5-chloro-2-thienyl)-sulfonyl | JA 43 |

TABLE 1-continued

| R₃ | R₄ | R₉ | R₁₉ | R₂₁ | R₂₂ | Denoted |
|----|----|----|----|----|----|---------|
| H | cyclo-propyl | H | H | H | 2-pyrazinyl | JA 46 |
| H | cyclo-propyl | H | H | H | {4-fluoro-[(4-fluoro-phenyl)-sulfonyl]-anilino}-carbothioyl | JA 53-2 |
| H | cyclo-propyl | H | H | H | {4-fluoro-[(4-nitro-phenyl)-sulfonyl]-anilino}-carbothioyl | JA 53-3 |
| H | cyclo-propyl | H | H | H | [(6-chloro-2-pyrazinyl)-4-fluoro-anilino]-carbothioyl | JA 53-5 |
| H | cyclo-propyl | H | H | H | [(6-chloro-2-pyridinyl)-4-fluoro-anilino]-carbothioyl | JA 53-6 |

B626:

6-fluoro-1-(4-fluorophenyl)-7-{4-[(4-nitroanilino)carbothioyl]-1-piperazinyl}-4-oxo-1,4-dihydro-3-quinolinecarboxylic acid;

B628:

6,8-difluoro-1-(2-fluoroethyl)-7-{4-[(4-nitroanilino)carbothioyl]-1-piperazinyl}-4-oxo-1,4-dihydro-3-quinolinecarboxylic acid;

B629:

1-cyclopropyl-6-fluoro-5-methyl-7-{3-methyl-4-[(4-nitroanilino)carbothioyl]-1-piperazinyl}-4-oxo-1,4-dihydro-3-quinolinecarboxylic acid;

B630:

1-ethyl-6,8-difluoro-7-{3-methyl-4-[(4-nitroanilino)carbothioyl]-1-piperazinyl}-4-oxo-1,4-dihydro-3-quinolinecarboxylic acid;

B633:

5-amino-1-cyclopropyl-6,8-difluoro-7-{4-[(4-nitroanilino)carbothioyl]-1-piperazinyl}-4-oxo-1,4-dihydro-3-quinolinecarboxylic acid;

B634:

1-(2,4-difluorophenyl)-6-fluoro-7-{3-methyl-4-[(4-nitroanilino)carbothioyl]-1-piperazinyl}-4-oxo-1,4-dihydro-3-quinolinecarboxylic acid;

B635:

1-(2,4-difluorophenyl)-6-fluoro-7-[3-methyl-4-({4-nitro[(4-nitrophenyl)sulfonyl]anilino}carbothioyl)-1-piperazinyl]-4-oxo-1,4-dihydro-3-quinolinecarboxylic acid;

B636:

7-[4-(anilinocarbothioyl)-3-methyl-1-piperazinyl]-1-ethyl-6,8-difluoro-4-oxo-1,4-dihydro-3-quinolinecarboxylic acid;

B637:

1-cyclopropyl-6-fluoro-7-{4-[(4-fluoroanilino)carbothioyl]-1-piperazinyl}-4-oxo-1,4-dihydro-3-quinolinecarboxylic acid;

B638:

1-ethyl-6-fluoro-7-{4-[(4-nitroanilino)carbothioyl]-1-piperazinyl}-4-oxo-1,4-dihydro-3-quinolincecarboxylic acid;

JAP 203:

6-fluoro-1-(4-fluorophenyl)-7-{4-[4-nitrophenyl)sulfonyl]-1-piperazinyl}-4-oxo-1,4-dihydro-3-quinolinecarboxylic acid;

JAP 204:

7-[4-(6-chloro-2-pyridinyl)-1-piperazinyl]-6-fluoro-1-(4-fluorophenyl)-4-oxo-1,4-dihydro-3-quinolinecarboxylic acid;

JAP 205:

7-[4-(6-chloro-2-pyrazinyl)-1-piperazinyl]-6-fluoro-1-(4-fluorophenyl)-4-oxo-1,4-dihydro-3-quinolinecarboxylic acid;

JAP 206:

6,8-difluoro-1-(2-fluoroethyl)-7-{4[(4-nitrophenyl)sulfonyl]-1-piperazinyl}-4-oxo-1,4-dihydro-3-quinolinecarboxylic acid;

JAP 207:

7-[4-(6-chloro-2-pyridinyl)-1-piperazinyl]-6,8-difluoro-1-(2-fluoroethyl)-4-oxo-1,4-dihydro-3-quinolinecarboxylic acid;

JAP 208:

7-[4-(6-chloro-2-pyrazinyl)-1-piperazinyl]-6,8-difluoro-1-(2-fluoroethyl)-4-oxo-1,4-dihydro-3-quinolinecarboxylic acid;

JAP 209:

1-cyclopropyl-6-fluoro-5-methyl-7-{3-methyl-4-[(4-nitrophenyl)sulfonyl]-1-piperazinyl}-4-oxo-1,4-dihydro-3-quinolinecarboxylic acid;

JAP 210:

7-[4-(6-chloro-2-pyridinyl)-3-methyl-1-piperazinyl]-1-cyclopropyl-6-fluoro-5-methyl-4-oxo-1,4-dihydro-3-quinolinecarboxylic acid;

JAP 211:

7-[4-(6-chloro-2-pyrazinyl)-3-methyl-1-piperazinyl]-1-cyclopropyl-6-fluoro-5-methyl-4-oxo-1,4-dihydro-3-quinolinecarboxylic acid;.

JAP 213:

1-ethyl-6,8-difluoro-7-{3-methyl-4-[(4-nitrophenyl)sulfonyl]-1-piperazinyl}-4-oxo-1,4-dihydro-3-quinolinecarboxylic acid;

JAP 214:

7-[4-(6-chloro-2-pyridinyl)-3-methyl-1-piperazinyl]-1-ethyl-6,8-difluoro-4-oxo-1,4-dihydro-3-quinolinecarboxylic acid;

JAP 221:

1-cyclopropyl-6,8-difluoro-5-{[(4-nitrophenyl)sulfonyl]amino}-7-{4-[(4-nitrophenyl)sulfonyl]-1-piperazinyl}-4-oxo-1,4-dihydro-3-quinolinecarboxylic acid;

JAP 222:

1-cyclopropyl-7-{3,5-dimethyl-4-[(4-nitrophenyl)sulfonyl]-1-piperazinyl}-6,8-difluoro-5-{[(4-nitrophenyl)sulfonyl]amino}-4-oxo-1,4-dihydro-3-quinolinecarboxylic acid;

JAP 223:

5-[(6-chloro-2-pyridinyl)amino]-7-[4-(6-chloro-2-pyridinyl)-3,5-dimethyl-1-piperazinyl]-1-cyclopropyl-6,8-difluoro-4-oxo-1,4-dihydro-3-quinolinecarboxylic acid;

JAP 224:

5-[(6-chloro-2-pyrazinyl)amino]-7-[4-(6-chloro-2-pyrazinyl)-3,5-dimethyl-1-piperazinyl]-1-cyclopropyl-6,8-difluoro-4-oxo-1,4-dihydro-3-quinolinecarboxylic acid;

JAP 225:

1-(2,4-difluorophenyl)-6-fluoro-7-{3-methyl-4-[(4-nitrophenyl)sulfonyl]-1-piperazinyl}-4-oxo-1,4-dihydro-3-quinolinecarboxylic acid;

JAP 226:

7-[4-(6-chloro-2-pyrazinyl)-3-methyl-1-piperazinyl]-1-(2,4-difluorophenyl)-6-fluoro-4-oxo-1,4-dihydro-3-quinolinecarboxylic acid;

JAP 227:

7-[4-(6-chloro-2-pyridinyl)-3-methyl-1-piperazinyl]-1-(2,4-difluorophenyl)-6-fluoro-4-oxo-1,4-dihydro-3-quinolinecarboxylic acid;

JA 1:

1-cyclopropyl-6-fluoro-4-oxo-7-[4-(phenylsulfonyl)-1-piperazinyl]-1,4-dihydro-3-quinolinecarboxylic acid;

JA 2:

1-cyclopropyl-6-fluoro-7-{4-[(4-methylphenyl)sulfonyl]-1-piperazinyl}-4-oxo-1,4-dihydro-3-quinolinecarboxylic acid;

JA 3:

1-cyclopropyl-6-fluoro-7-{4-[(4-nitrophenyl)sulfonyl]-1-piperazinyl}-4-oxo-1,4-dihydro-3-quinolinecarboxylic acid;

JA 4:

1-cyclopropyl-6-fluoro-7-{4-[(4-methoxyphenyl)sulfonyl]-1-piperazinyl}-4-oxo-1,4-dihydro-3-quinolinecarboxylic acid;

JA 5:

1-cyclopropyl-6-fluoro-7-[4-(2-naphthylsulfonyl)-1-piperazinyl]-4-oxo-1,4-dihydro-3-quinolinecarboxylic acid;

JA 6:

1-cyclopropyl-6-fluoro-7-[4-(mesitylsulfonyl)-1-piperazinyl]-4-oxo-1,4-dihydro-3-quinolinecarboxylic acid;

JA 7:

1-cyclopropyl-6-fluoro-4-oxo-7-[4-(propylsulfonyl)-1-piperazinyl]-1,4-dihydro-3-quinolinecarboxylic acid;

JA 9:

7-[4-(benzylsulfonyl)-1-piperazinyl]-1-cyclopropyl-6-fluoro-4-oxo-1,4-dihydro-3-quinolinecarboxylic acid;

JA 10:

1-cyclopropyl-6-fluoro-7-[4-(methylsulfonyl)-1-piperazinyl]-4-oxo-1,4-dihydro-3-quinolinecarboxylic acid;

JA 12:

1-cyclopropyl-6-fluoro-4-oxo-7-{4-[(trifluoromethyl)sulfonyl]-1-piperazinyl}-1,4-dihydro-3-quinolinecarboxylic acid;

JA 13:

7-{4-[(5-bromo-2-thienyl)sulfonyl]-1-piperazinyl}-1-cyclopropyl-6-fluoro-4-oxo-1,4-dihydro-3-quinolinecarboxylic acid;

JA 14:

1-cyclopropyl-7-{4-[(3,5-dichloro-2-hydroxyphenyl)sulfonyl]-1-piperazinyl}-6-fluoro-4-oxo-1,4-dihydro-3-quinolinecarboxylic acid;

JA 20:

1-ethyl-6-fluoro-7-{4-[(4-nitrophenyl)sulfonyl]-1-piperazinyl}-4-oxo-1,4-dihydro-3-quinolinecarboxylic acid;

JA 21:

1-ethyl-6-fluoro-7-{4-[(4-methoxyphenyl)sulfonyl]-1-piperazinyl}-4-oxo-1,4-dihydro-3-quinolinecarboxylic acid;

JA 26:

7-[4-(benzylsulfonyl)-1-piperazinyl]-1-ethyl-6-fluoro-4-oxo-1,4-dihydro-3-quinolinecarboxylic acid;

JA 31:

7-{4-[(3,5-dichloro-2-hydroxyphenyl)sulfonyl]-1-piperazinyl}-1-ethyl-6-fluoro-4-oxo-1,4-dihydro-3-quinolinecarboxylic acid;

JA 39:

7-[4-(6-chloro-2-pyrazinyl)-1-piperazinyl]-1-cyclopropyl-6-fluoro-4-oxo-1,4-dihydro-3-quinolinecarboxylic acid;

JA 40:

7-[4-(5-bromo-2-pyridinyl)-1-piperazinyl]-1-cyclopropyl-6-fluoro-4-oxo-1,4-dihydro-3-quinolinecarboxylic acid;

JA 42:

7-[4-(6-chloro-2-pyridinyl)-1-piperazinyl]-1-cyclopropyl-6-fluoro-4-oxo-1,4-dihydro-3-quinolinecarboxylic acid;

JA 43:

7-{4-[(5-chloro-2-thienyl)sulfonyl]-1-piperazinyl}-1-cyclopropyl-6-fluoro-4-oxo-1,4-dihydro-3-quinolinecarboxylic acid;

JA 46:

1-cyclopropyl-6-fluoro-4-oxo-7-[4-(2-pyrazinyl)-1-piperazinyl]-1,4-dihydro-3-quinolinecarboxylic acid.

In another preferred embodiment of the present invention, $R_9$ is a C—Y bond and $R_4$ is a C—C bond to said radical —YCR$_{10}$R$_{11}$CR$_{12}$R$_{13}$—. Typically, R$_{10}$–R$_{13}$ are H, or R$_{10}$–R$_{12}$ are H and R$_{13}$ is methyl.

In another one of the most preferred embodiments, a compound according to the present invention has the general formula (III):

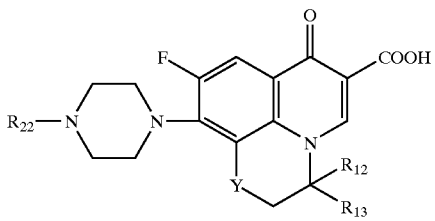

(III)

wherein R$_{12}$, R$_{13}$ and R$_{22}$ are as previously defined.

Preferably, Y is either S or O.

Preferably, R$_{12}$ and R$_{13}$ are independently either H or CH$_3$.

Preferably, R$_{22}$ is selected from the same said group of substituents as that preferred in the compound(s) of the general formula (II) supra.

Most preferably, a compound according to the formula (III) is selected from the compounds disclosed in the following Table 2, the systematic names of which are also given hereinbelow:

TABLE 2

| Y | R$_{12}$ | R$_{13}$ | R$_{22}$ | Denoted |
|---|---|---|---|---|
| O | H | CH$_3$ | (4-nitrophenyl)sulfonyl | JAP 215 |
| O | H | CH$_3$ | 6-chloro-2-pyridinyl | JAP 216 |
| O | H | CH$_3$ | 6-chloro-2-pyrazinyl | JAP 217 |
| S | H | H | (4-nitrophenyl)sulfonyl | JAP 218 |
| S | H | H | 6-chloro-2-pyridinyl | JAP 219 |
| S | H | H | 6-chloro-2-pyrazinyl | JAP 220 |
| O | H | CH$_3$ | (4-nitroanilino)carbothioyl | B631 |
| S | H | H | (4-nitroanilino)carbothioyl | B632 |

JAP 215:

9-fluoro-3-methyl-10-{4-[(4-nitrophenyl)sulfonyl]-1-piperazinyl}-7-oxo-2,3-dihydro-7H-[1,4]oxazino[2,3,4-ij]quinoline-6-carboxylic acid;

JAP 216:

10-[4-(6-chloro-2-pyridinyl)-1-piperazinyl]-9-fluoro-3-methyl-7-oxo-2,3-dihydro-7H-[1,4]oxazino[2,3,4-ij]quinoline-6-carboxylic acid;

JAP 217:

10-[4-(6-chloro-2-pyrazinyl)-1-piperazinyl]-9-fluoro-3-methyl-7-oxo-2,3-dihydro-7H-[1,4]oxazino[2,3,4-ij]quinoline-6-carboxylic acid;

JAP 218:

9-fluoro-10-{4-[(4-nitrophenyl)sulfonyl]-1-piperazinyl}-7-oxo-2,3-dihydro-7H-[1,4]thiazino[2,3,4-ij]quinoline-6-carboxylic acid;

JAP 219:

10-[4-(6-chloro-2-pyridinyl)-1-piperazinyl]-9-fluoro-7-oxo-2,3-dihydro-7H-[1,4]thiazino[2,3,4-ij]quinoline-6-carboxylic acid;

JAP 220:

10-[4-(6-chloro-2-pyrazinyl)-1-piperazinyl]-9-fluoro-7-oxo-2,3-dihydro-7H-[1,4]thiazino[2,3,4-ij]quinoline-6-carboxylic acid;

B631:

9-fluoro-3-methyl-10-{4-[(4-nitroanilino)carbothioyl]-1-piperazinyl}-7-oxo-2,3-dihydro-7H-[1,4]oxazino[2,3,4-ij]quinoline-6-carboxylic acid;

B632:

9-fluoro-10-{4-[(4-nitroanilino)carbothioyl]-1-piperazinyl}-7-oxo-2,3-dihydro-7H-[1,4]thiazino[2,3,4-ij]quinoline-6-carboxylic acid.

In another preferred embodiment of the present invention, R$_5$ and R$_6$ are selected from the group of substituents (a)–(m). Here, R$_4$ is typically cyclopropyl.

In yet another one of the most preferred embodiments, a compound according to the present invention has the general formula (IV):

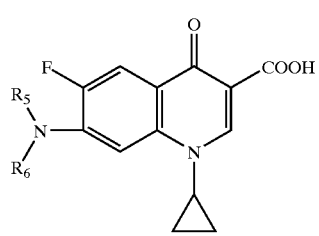

(IV)

wherein R$_5$ and R$_6$ are as previously defined.

Preferably, R$_5$ and R$_6$ are independently selected from H and at least one of the same said group of substituents as that preferred for R$_{22}$ in the compound(s) of the general formula (II) supra.

Most preferably, a compound according to the formula (IV) is selected from the compounds disclosed in the following Table 3, the systematic names of which are also given hereinbelow:

TABLE 3

| R$_5$ | R$_6$ | Denoted |
|---|---|---|
| {4-fluorophenyl}-sulfonyl | 6-{[(4-fluorophenyl)-sulfonyl]amino}-2-pyridinyl | JA 47-2 |
| H | 5-bromo-2-pyridinyl | JA 61 |
| H | 4-pyridinylmethyl | JA 68 |
| H | 4-carboxycyclohexyl | JA 69 |
| 6-chloro-2-pyrazinyl | 4-carboxycyclohexyl | JA 69-2 |
| (trifluoromethyl)-sulfonyl | 4-carboxycyclohexyl | JA 69-3 |
| H | 4-carboxybenzyl | JA 70 |
| H | tetrahydro-2-furanylmethyl | JA 73 |
| H | 4-isopropylphenyl | JA 74 |
| H | 2-(1-piperidinyl)ethyl | JA 76 |
| (4-nitrophenyl)-sulfonyl | 2-(1-piperidinyl)ethyl | JA 76-2 |
| 6-chloro-2-pyrazinyl | 2-(1-piperidinyl)ethyl | JA 76-3 |
| (4-fluorophenyl)-sulfonyl | 2-[(2-{[(4-fluorophenyl)-sulfonyl]amino}ethyl)di-sulfanyl]ethyl | JA 79-2 |
| (4-nitrophenyl)-sulfonyl | 2-[(2-{[(4-nitrophenyl)-sulfonyl]amino}ethyl)di-sulfanyl]ethyl | JA 79-3 |
| (4-nitrophenyl)-sulfonyl | 2-[2-({[(4-nitrophenyl)-sulfonyl]amino}methoxy)-ethoxy]ethyl | JA 82-2 |
| 6-chloro-2-pyrazinyl phenylsulfonyl | 2-(2-{[(6-chloro-2-pyrazinyl)-amino]methoxy}ethoxy)ethyl | JA 82-3 |
|  | 4-pyridinylmethyl | JA 91 |
| H | 2-(1-pyrrolidinyl)ethyl | JA 97 |
| (4-nitroanilino)-carbothioyl | 2-(1-pyrrolidinyl)ethyl | JA 97-2 |

TABLE 3-continued

| R₅ | R₆ | Denoted |
|---|---|---|
| 6-chloro-2-pyrazinyl | 2-(1-pyrrolidinyl)ethyl | JA 97-3 |
| (4-nitrophenyl)-sulfonyl | 2-(1-pyrrolidinyl)ethyl | JA 97-4 |
| (trifluoromethyl)-sulfonyl | 2-(1-pyrrolidinyl)ethyl | JA 97-5 |
| (4-fluorophenyl)-sulfonyl | [3-({[(4-fluorophenyl)-sulfonyl]amino}methyl)-cyclohexyl]methyl | JA 99-2 |
| H | 3-[(3-aminopropyl)(methyl)-amino]propyl | JA 102 |
| H | 3-aminopropyl | JA 103 |
| (trifluoromethyl)-sulfonyl | 3-{[(trifluoromethyl)-sulfonyl]amino}propyl | JA 103-2 |
| (4-nitrophenyl)-sulfonyl | 3-{[(4-nitrophenyl)-sulfonyl]amino}propyl | JA 103-3 |
| (trifluoromethyl)-sulfonyl | 3-(dimethylamino)-2,2-dimethylpropyl | JA 104-2 |
| 2-thienylcarbonyl | 3-(dimethylamino)-2,2-dimethylpropyl | JA 104-3 |
| H | 2-aminocyclohexyl | JA 105 |
| (trifluoromethyl)-sulfonyl | 2-{[(trifluoromethyl)-sulfonyl]amino}ethyl | JA 106-3 |
| (4-nitrophenyl)-sulfonyl | 2-{[(4-nitrophenyl)-sulfonyl]amino}ethyl | JA 106-4 |
| (trifluoromethyl)-sulfonyl | 2,2-dimethyl-3-{[(trifluoro-methyl)sulfonyl]amino}propyl | JA 107-2 |
| (4-nitrophenyl)-sulfonyl | tetrahydro-2-furanylmethyl | JA 117 |
| 2-thienylcarbonyl | 2-furylmethyl | JA 124 |
| 2-thienylcarbonyl | 2-(1-piperidinyl)ethyl | JA 128 |
| (4-methoxyphenyl)-sulfonyl | tetrahydro-2-furanylmethyl | JA 135 |
| 2-naphtylsulfonyl | tetrahydro-2-furanylmethyl | JA 136 |
| phenethylsulfonyl | tetrahydro-2-furanylmethyl | JA 137 |
| (trifluoromethyl)-sulfonyl | tetrahydro-2-furanylmethyl | JA 138 |
| phenylsulfonyl | tetrahydro-2-furanylmethyl | JA 139 |
| 2-thienylcarbonyl | tetrahydro-2-furanylmethyl | JA 140 |
| 6-chloro-2-pyrazinyl | tetrahydro-2-furanylmethyl | JA 141 |
| 5-bromo-2-pyridinyl | tetrahydro-2-furanylmethyl | JA 142 |
| 6-chloro-2-pyridinyl | tetrahydro-2-furanylmethyl | JA 143 |
| acetoacetyl | tetrahydro-2-furanylmethyl | JA 144 |
| 2-(4-pyridinyl)-ethyl | tetrahydro-2-furanylmethyl | JA 145 |
| 2-(2-pyridinyl)-ethyl | tetrahydro-2-furanylmethyl | JA 146 |
| acetoacetyl | 2-methoxy-1-methylethyl | JA 148 |
| (4-nitrophenyl)-sulfonyl | 2-methoxy-1-methylethyl | JA 149 |
| (4-nitrophenyl)-sulfonyl | 4-pyridinylmethyl | JA 156 |
| (4-nitrophenyl)-sulfonyl | 5-bromo-2-pyridinyl | JA 158 |
| (4-fluorophenyl)-sulfonyl | 5-bromo-2-pyridinyl | JA 159 |
| (trifluoromethyl)-sulfonyl | 5-bromo-2-pyridinyl | JA 160 |
| 2-naphtylsulfonyl | 5-bromo-2-pyridinyl | JA 161 |
| 2-naphtylsulfonyl | tetrahydro-2-furanylmethyl | JA 162 |
| 2-naphtylsulfonyl | 4-pyridinylmethyl | JA 163 |
| (trifluoromethyl)-sulfonyl | 4-pyridinylmethyl | JA 164 |
| 6-chloro-2-pyridinyl | 4-pyridinylmethyl | JA 165 |
| 6-chloro-2-pyrazinyl | 4-pyridinylmethyl | JA 166 |
| 5-bromo-2-pyridinyl | 4-pyridinylmethyl | JA 167 |
| (4-nitrophenyl)-sulfonyl | 4-carboxybenzyl | JA 168 |
| 2-naphtylsulfonyl | 4-carboxybenzyl | JA 169 |
| (trifluoromethyl)-sulfonyl | 4-carboxybenzyl | JA 170 |
| 6-chloro-2-pyridinyl | 4-carboxybenzyl | JA 171 |
| 6-chloro-2-pyrazinyl | 4-carboxybenzyl | JA 172 |
| 5-bromo-2-pyridinyl | 4-carboxybenzyl | JA 173 |

JA 61:

7-[(5-bromo-2-pyridinyl)amino]-1-cyclopropyl-6-fluoro-4-oxo-1,4-dihydro-3-quinolinecarboxylic acid;

JA 68:

1-cyclopropyl-6-fluoro-4-oxo-7-[(4-pyridinylmethyl)amino]-1,4-dihydro-3-quinolinecarboxylic acid;

JA 69:

7-[(4-carboxycyclohexyl)amino]-1-cyclopropyl-6-fluoro-4-oxo-1,4-dihydro-3-quinolinecarboxylic acid;

JA 70:

7-[(4-carboxybenzyl)amino]-1-cyclopropyl-6-fluoro-4-oxo-1,4-dihydro-3-quinolinecarboxylic acid;

JA 73:

1-cyclopropyl-6-fluoro-4-oxo-7-[(tetrahydro-2-furanylmethyl)amino]-1,4-dihydro-3-quinolinecarboxylic acid;

JA 74:

1-cyclopropyl-6-fluoro-7-(4-isopropylanilino)-4-oxo-1,4-dihydro-3-quinolinecarboxylic acid;

JA 76:

1-cyclopropyl-6-fluoro-4-oxo-7-{[2-(1-piperidinyl)ethyl]-amino}-1,4-dihydro-3-quinolinecarboxylic acid;

JA 91:

1-cyclopropyl-6-fluoro-4-oxo-7-[(phenylsulfonyl)(4-pyridinylmethyl)amino]-1,4-dihydro-3-quinolinecarboxylic acid;

JA 103:

7-[(3-aminopropyl)amino]-1-cyclopropyl-6-fluoro-4-oxo-1,4-dihydro-3-quinolinecarboxylic acid;

JA 105:

7-[(2-aminocyclohexyl)amino]-1-cyclopropyl-6-fluoro-4-oxo-1,4-dihydro-3-quinolinecarboxylic acid;

JA 117:

1-cyclopropyl-6-fluoro-7-[[(4-nitrophenyl)sulfonyl](tetrahydro-2-furanylmethyl)amino]-4-oxo-1,4-dihydro-3-quinolinecarboxylic acid;

JA 135:

1-cyclopropyl-6-fluoro-7-[[(4-methoxyphenyl)sulfonyl](tetrahydro-2-furanylmethyl)amino]-4-oxo-1,4-dihydro-3-quinolinecarboxylic acid;

JA 136:

1-cyclopropyl-6-fluoro-7-[(2-naphthylsulfonyl)(tetrahydro-2-furanylmethyl)amino]-4-oxo-1,4-dihydro-3-quinolinecarboxylic acid;

JA 137:

1-cyclopropyl-6-fluoro-4-oxo-7-[(phenethylsulfonyl)(tetrahydro-2-furanylmethyl)amino]-1,4-dihydro-3-quinolinecarboxylic acid;

JA 138:

1-cyclopropyl-6-fluoro-4-oxo-7-{(tetrahydro-2-furanylmethyl)[(trifluoromethyl) sulfonyl]amino}-1,4-dihydro-3-quinolinecarboxylic acid;

JA 139:

1-cyclopropyl-6-fluoro-4-oxo-7-[(phenylsulfonyl)(tetrahydro-2-furanylmethyl)amino]-1,4-dihydro-3-quinolinecarboxylic acid;

JA 141:

7-[(6-chloro-2-pyrazinyl)(tetrahydro-2-furanylmethyl)amino]-1-cyclopropyl-6-fluoro-4-oxo-1,4-dihydro-3-quinolinecarboxylic acid;

JA 142:

7-[(5-bromo-2-pyridinyl)(tetrahydro-2-furanylmethyl)amino]-1-cyclopropyl-6-fluoro-4-oxo-1,4-dihydro-3-quinolinecarboxylic acid;

JA 143:

7-[(6-chloro-2-pyridinyl)(tetrahydro-2-furanylmethyl)amino]-1-cyclopropyl-6-fluoro-4-oxo-1,4-dihydro-3-quinolinecarboxylic acid;

JA 144:

7-[acetoacetyl tetrahydro-2-furanylmethyl)amino]-1-cyclopropyl-6-fluoro-4-oxo-1,4-dihydro-3-quinolinecarboxylic acid;

JA 145:

1-cyclopropyl-6-fluoro-4-oxo-7-[[2-(4-pyridinyl)ethyl](tetrahydro-2-furanylmethyl)amino]-1,4-dihydro-3-quinolinecarboxylic acid;

JA 146:

1-cyclopropyl-6-fluoro-4-oxo-7-[[2-(2-pyridinyl)ethyl](tetrahydro-2-furanylmethyl)amino]-1,4-dihydro-3-quinolinecarboxylic acid;

JA 156:

1-cyclopropyl-6-fluoro-7-[[4-nitrophenyl)sulfonyl](4-pyridinylmethyl)amino]-4-oxo-1,4-dihydro-3-quinolinecarboxylic acid;

JA 158:

7-{(5-bromo-2-pyridinyl)[(4-nitrophenyl)sulfonyl]amino}-1-cyclopropyl-6-fluoro-4-oxo-1,4-dihydro-3-quinolinecarboxylic acid;

JA 159:

7-{(5-bromo-2-pyridinyl)[(4-fluorophenyl)sulfonyl]amino}-1-cyclopropyl-6-fluoro-4-oxo-1,4-dihydro-3-quinolinecarboxylic acid;

JA 160:

7-{(5-bromo-2-pyridinyl)[(trifluoromethyl)sulfonyl]amino}-1-cyclopropyl-6-fluoro-4-oxo-1,4-dihydro-3-quinolinecarboxylic acid;

JA 161:

7-[(5-bromo-2-pyridinyl)(2-naphtylsulfonyl)amino]-1-cyclopropyl-6-fluoro-4-oxo-1,4-dihydro-3-quinolinecarboxylic acid;

JA 162:

1-cyclopropyl-6-fluoro-7-[(2-naphtylsulfonyl)(tetrahydro-2-furanylmethyl)amino]-4-oxo-1,4-dihydro-3-quinolinecarboxylic acid;

JA 163:

1-cyclopropyl-6-fluoro-7-[(2-naphtylsulfonyl)(4-pyridinylmethyl)amino]-4-oxo-1,4-dihydro-3-quinolinecarboxylic acid;

JA 164:

1-cyclopropyl-6-fluoro-4-oxo-7-{(4-pyridinylmethyl)[(trifluoromethyl)sulfonyl]amino}-1,4-dihydro-3-quinolinecarboxylic acid;

JA 165:

7-[(6-chloro-2-pyridinyl)(4-pyridinylmethyl)amino]-1-cyclopropyl-6-fluoro-4-oxo-1,4-dihydro-3-quinolinecarboxylic acid;

JA 166:

7-[(6-chloro-2-pyrazinyl)(4-pyridinylmethyl)amino]-1-cyclopropyl-6-fluoro-4-oxo-1,4-dihydro-3-quinolinecarboxylic acid;

JA 167:

7-[(5-bromo-2-pyridinyl)(4-pyridinylmethyl)amino]-1-cyclopropyl-6-fluoro-4-oxo-1,4-dihydro-3-quinolinecarboxylic acid;

JA 168:

7-{(4-carboxybenzyl)[(4-nitrophenyl)sulfonyl]amino}-1-cyclopropyl-6-fluoro-4-oxo-1,4-dihydro-3-quinolinecarboxylic acid;

JA 169:

7-[(4-carboxybenzyl)(2-naphtylsulfonyl)amino]-1-cyclopropyl-6-fluoro-4-oxo-1,4-dihydro-3-quinolinecarboxylic acid;

JA 170:

7-{(4-carboxybenzyl)[(trifluoromethyl)sulfonyl]amino}-1-cyclopropyl-6-fluoro-4-oxo-1,4-dihydro-3-quinolinecarboxylic acid;

JA 171:

7-[(4-carboxybenzyl)(6-chloro-2-pyridinyl)amino]-1-cyclopropyl-6-fluoro-4-oxo-1,4-dihydro-3-quinolinecarboxylic acid;

JA 172:

7-[(4-carboxybenzyl)(6-chloro-2-pyrazinyl)amino]-1-cyclopropyl-6-fluoro-4-oxo-1,4-dihydro-3-quinoline-carboxylic acid;

JA 173:

7-[(5-bromo-2-pyridinyl)(4-carboxybenzyl)amino]-1-cyclopropyl-6-fluoro-4-oxo-1,4-dihydro-3-quinolinecarboxylic acid.

In another preferred embodiment of the present invention, $R_5$ and $R_6$ form said group (o).

In still another one of the most preferred embodiments, a compound according to the present invention has the general formula (V):

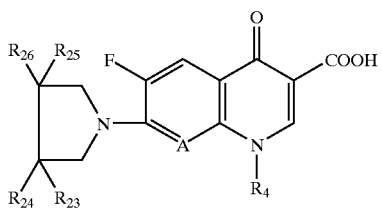

(V)

wherein $R_4$, A and $R_{23}$–$R_{26}$ are as previously defined.

Preferably, A is selected from —CCl—, —COCH$_3$—, and —N—.

Preferably, $R_4$ is selected from a group of substituents consisting of cyclopropyl, ethyl, 2-fluoroethyl, 4-fluorophenyl and 2,4-difluorophenyl.

Preferably, $R_{23}$–$R_{26}$ are independently selected from H and at least one of a group of substituents consisting of fluoromethyl, methoxyimino, (6-chloro-2-pyridinyl)amino, (6-chloro-2-pyridinyl) [(4-nitrophenyl)sulfonyl]amino, (6-chloro-2-pyrazinyl) [(4-nitrophenyl)sulfonyl]amino, [(4-nitroanilino)carbothioyl]amino, {[(4-nitrophenyl)sulfonyl]amino}methyl, [(6-chloro-2-pyrazinyl)amino]methyl, [(6-chloro-2-pyridinyl)amino]methyl, {[(4-fluoroanilino)carbothioyl]amino}methyl, {({4-fluoro[(4-nitrophenyl)sulfonyl]anilino}carbothioyl) [(4-nitrophenyl)sulfonyl]amino}methyl, {({4-fluoro[(4-methoxyphenyl)sulfonyl]anilino}carbothioyl) [(4-methoxyphenyl)sulfonyl]amino}methyl and the group of substituents preferred for $R_{22}$ in the compound(s) of the general formula (II) supra.

Most preferably, a compound according to the formula (V) is selected from the compounds disclosed in the following Table 4, the systematic names of which are also given hereinbelow:

TABLE 4

| $R_4$ | A | $R_{23}$ | $R_{24}$ | $R_{25}$ | $R_{26}$ | Denoted |
|---|---|---|---|---|---|---|
| cyclopropyl | —CCl— | H | H | H | (6-chloro-2-pyridinyl)amino | JAP 200 |
| cyclopropyl | —CCl— | H | H | H | (6-chloro-2-pyridinyl)-[(4-nitrophenyl)-sulfonyl]amino | JAP 201 |
| cyclopropyl | —CCl— | H | H | H | (6-chloro-2-pyrazinyl)[(4-nitrophenyl)-sulfonyl]amino | JAP 202 |
| cyclopropyl | —CCl— | H | H | H | [(4-nitroanilino)-carbothioyl]amino | B627 |
| cyclopropyl | —COCH$_3$— | H | H | CH$_2$F | {[(4-nitrophenyl)-sulfonyl]amino}-methyl | JA 1006 |
| cyclopropyl | —COCH$_3$— | H | H | CH$_2$F | [(6-chloro-2-pyrazinyl)amino]-methyl | JA 1007 |
| cyclopropyl | —COCH$_3$— | H | H | CH$_2$F | [(6-chloro-2-pyridinyl)amino]-methyl | JA 1008 |
| cyclopropyl | —COCH$_3$— | H | H | CH$_2$F | {[(4-fluoroanilino)-carbothioyl]-amino}methyl | JA 1009 |
| cyclopropyl | —COCH$_3$— | H | H | CH$_2$F | {[(4-fluoro[(4-nitrophenyl)sulfonyl]-anilino}carbothioyl)-{(4-nitrophenyl)-sulfonyl]-amino}methyl | JA 1010 |
| cyclopropyl | —N— | =NOCH$_3$ | H | | [(6-chloro-2-pyrazinyl)amino]-methyl | JA 1012 |
| cyclopropyl | —N— | =NOCH$_3$ | H | | {({4-fluoro[(4-methoxyphenyl)-sulfonyl]anilino}-carbothioyl)[(4-methoxyphenyl)-sulfonyl]amino}methyl | JA 1013 |

JAP 200:

8-chloro-7-{3-[(6-chloro-2-pyridinyl)amino]-1-pyrrolidinyl}-1-cyclopropyl-6-fluoro-4-oxo-1,4-dihydro-3-quinolinecarboxylic acid;

JAP 201:

8-chloro-7-(3-{(6-chloro-2-pyridinyl)[(4-nitrophenyl)sulfonyl]amino}-1-pyrrolidinyl)-1-cyclopropyl-6-fluoro-4-oxo-1,4-dihydro-3-quinolinecarboxylic acid;

JAP 202:

8-chloro-7-(3-{(6-chloro-2-pyrazinyl) [(4-nitrophenyl)sulfonyl]amino)-1-pyrrolidinyl}-1-cyclopropyl-6-fluoro-4-oxo-1,4-dihydro-3-quinolinecarboxylic acid;

B627:

8-chloro-1-cyclopropyl-6-fluoro-7-(3-{[(4-nitroanilino)carbothioyl]amino}-1-pyrrolidinyl)-4-oxo-1,4-dihydro-3-quinolinecarboxylic acid;

JA 1006:

1-cyclopropyl-6-fluoro-7-[3-(fluoromethyl)-3-{[(4-nitrophenyl)sulfonyl]amino}methyl)-1-pyrrolidinyl-8-methoxy-4-oxo-1,4-dihydro-3-quinolinecarboxylic acid;

JA 1007:

7-[3-{[(6-chloro-2-pyrazinyl)amino]methyl}-3-(fluoromethyl)-1-pyrrolidinyl-1-cyclopropyl-6-fluoro-8-methoxy-4-oxo-1,4-dihydro-3-quinolinecarboxylic acid;

JA 1008:

7-[3-{[(6-chloro-2-pyridinyl)amino]methyl}-3-(fluoromethyl)-1-pyrrolidinyl]-1-cyclopropyl-6-fluoro-8-methoxy-4-oxo-1,4-dihydro-3-quinolinecarboxylic acid;

JA 1009:

1-cyclopropyl-6-fluoro-7-[3-({[(4-fluoroanilino)carbothioyl]amino}methyl)-3-(fluoromethyl)-1-pyrrolidinyl]-8-methoxy-4-oxo-1,4-dihydro-3-quinolinecarboxylic acid;

JA 1010:

1-cyclopropyl-6-fluoro-7-[3-(fluoromethyl)-3-({({4-fluoro[(4-nitrophenyl)sulfonyl]anilino}carbothioyl)[(4-nitrophenyl)sulfonyl]amino}methyl)-1-pyrrolidinyl]-8-methoxy-4-oxo-1,4-dihydro-3-quinolinecarboxylic acid;

JA 1012:

7-[3-{[(6-chloro-2-pyrazinyl)amino]methyl}-4-(methoxyimino)-1-pyrrolidinyl]-1-cyclopropyl-6-fluoro-4-oxo-1,4-dihydro[1,8]naphtyridine-3-carboxylic acid;

JA 1013:

1-cyclopropyl-6-fluoro-7-[3-({({4-fluoro[(4-methoxyphenyl)sulfonyl]anilino}carbothioyl) [(4-methoxyphenyl)sulfonyl]amino}methyl)-4-(methoxyimino)-1-pyrrolidinyl]-4-oxo-1,4-dihydro[1,8]naphtyridine-3-carboxylic acid.

In another preferred embodiment of the present invention, $R_5$ and $R_6$ form said group (p).

Furthermore, in yet another one of the most preferred embodiments, a compound according to the present invention has the general formula (VI):

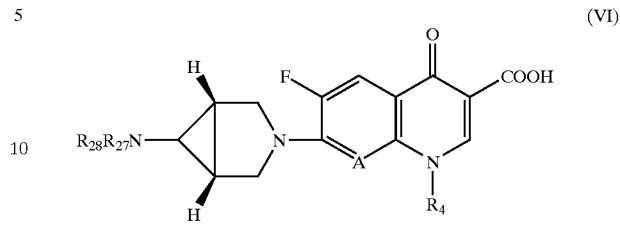

(VI)

wherein A, $R_4$, $R_{27}$ and $R_{28}$ are as previously defined.

Preferably, A is selected from —CCl—, —COCH$_3$—, and —N—.

Preferably, $R_4$ is selected from a group of substituent6 consisting of cyclopropyl, ethyl, 2-fluoroethyl, 4-fluorophenyl and 2,4-difluorophenyl.

Preferably, $R_{27}$ and $R_{28}$ are independently, selected from H and at least one of the same said group of substituents as that preferred for $R_{23}$–$R_{26}$ in the compound(s) of the general formula (V) supra.

Most preferably, a compound according to the formula (VI) is selected from the compounds disclosed in the following Table 5, the systematic names of which are also given hereinbelow:

TABLE 5

| A | $R_4$ | $R_{27}$ | $R_{29}$ | Denoted |
|---|---|---|---|---|
| —N— | 2,4-difluorophenyl | H | (4-fluorophenyl)sulfonyl | JA 1000 |
| —N— | 2,4-difluorophenyl | H | 6-chloro-2-pyridinyl | JA 1001 |
| —N— | 2,4-difluorophenyl | H | 6-chloro-2-pyrazinyl | JA 1002 |
| —N— | 2,4-difluorophenyl | H | (4-fluoroanilino)carbonyl | JA 1003 |
| —N— | 2,4-difluorophenyl | H | (4-fluoroanilino)carbothioyl | JA 1004 |
| —N— | 2,4-difluorophenyl | (4-nitrophenyl)sulfonyl | {4-fluoro[(4-nitrophenyl)sulfonyl]anilino}carbothioyl | JA 1005 |

JA 1000:

1-(2,4-difluorophenyl)-6-fluoro-7-(1R,5S)-6-{[(4-fluorophenyl)sulfonyl]amino}-3-azabicyclo[3.1.0]hex-3-yl)-4-oxo-1,4-dihydro1,8]naphtyridine-3-carboxylic acid;

JA 1001:

7-{(1R,5S)-6-[(6-chloro-2-pyridinyl)amino]-3-azabicyclo[3.1.0]hex-3-yl}-1-(2,4-difluorophenyl)-6-fluoro-4-oxo-1,4-dihydro[1,8]naphtyridine-3-carboxylic acid;

JA 1002:

7-{(1R,5S)-6-[(6-chloro-2-pyrazinyl)amino]-3-azabicyclo[3.1.0]hex-3-yl}-1-(2,4-difluorophenyl)-6-fluoro-4-oxo-1,4-dihydro[1,8]naphtyridine-3-carboxylic acid;

JA 1003:

1-(2,4-difluorophenyl)-6-fluoro-7-((1R,5S)-6-{[(4-fluoroanilino)carbonyl]amino}-3-azabicyclo[3.1.0]hex-3-yl)-4-oxo-1,4-dihydro[1,8]naphtyridine-3-carboxylic acid;

JA 1004:

1-(2,4-difluorophenyl)-6-fluoro-7-((1R,5S)-6-{[(4-fluoroanilino)carbothioyl]amino}-3-azabicyclo[3.1.0]hex-3-yl)-4-oxo-1,4-dihydro[1,8]naphtyridine-3-carboxylic acid;

JA 1005:

1-(2,4-difluorophenyl)-6-fluoro-7-((1R,5S)-6-{({4-fluoro[(4-nitrophenyl)-sulfonyl]anilino}carbothionyl)[(4-nitrophenyl)sulfonyl]amino}-3-azabicyclo[3.1.0]hex-3-yl)-4-oxo-1,4-dihydro[1,8]naphtyridine-3-carboxylic acid.

Furthermore, the present invention relates to a compound as set forth above for use as a pharmaceutical.

Accordingly, the present invention also relates to a pharmaceutical composition comprising a compound as set forth above as active ingredient in association with a pharmaceutically acceptable adjuvant, diluent or carrier.

Moreover, the present invention relates to an animal feed, food concentrate or drinking water comprising a compound as set forth above.

It should be noted that the composition and animal feed according to the present invention may optionally include two or more of the above outlined compounds.

In addition, the present invention relates to the use of a compound as defined above for the manufacture of a medicament for treatment of bacterial and parasitic disorders, particularly coccidiosis and disorders related thereto.

The present invention is also concerned with a method for treatment of bacterial and parasitic disorders, particularly coccidiosis and disorders related thereto, wherein said method comprises administering to an animal, preferably poultry, of a therapeutically effective amount of a compound as defined above.

Although the present compounds were shown to be especially suitable for treatment of coccidiodis (vide infra), it was anticipated that they are also therapeutically efficient against other protozoa, such as those set forth below as non-limiting examples:

Tryanosoma, such as *T. cruzi, T. brucei, T. congolense, T. evansi* and *T. simiae*;
Toxoplasma, such as *T. gondii*;
Plasmodium;
Babesia spp.;
Theileria spp.;
Leishmania, such as *L. tropica, L. major* and *L. donavani*;
Entaamoeba histolytica;
Giardia intestinalis;
Hexamita meleagridis;
Trichomonas spp.

*Trypanosoma* spp. is the cause of sleeping sickness in humans and animals, particularly in Africa. It is transmitted by the bite of the tsetse flies. It is well known that new compounds for treatment of *Trypanosoma* infections are an ongoing demand in the art.

Consequently, the present compounds were evaluated against *Trypanosoma* as well, and it was shown that they are also highly efficient for treatment of *Trypanosoma* parasites (vide infra).

Thus, the present invention also specifically relates to the use of the present compounds for the manufacture of a medicament for treatment of parasitic infection caused by *Trypanosoma*.

Accordingly, the present invention is also specifically concerned with a method for treatment of parasitic disorders caused by *Trypanosoma*, wherein said method comprises administering to an animal of a therapeutically effective amount of a compound as defined above.

The present compounds are also anticipated to be active against arthropods or helminth parasites, such as flatworms and nematodes. Typical examples of such parasites are disclosed in U.S. Pat. No. 5,863,775, the entire teachings of which are incorporated herein by reference.

The typical dosage of the compounds according to the present invention varies within a wide range and will depend on various factors such as the particular requirement of each receiving individual and the route of administration. The dosage is generally within the range of 0.01–1000 mg/kg animal feed or body weight.

The present invention is further illustrated by the following non-limiting experimental part.

Preparation of the Compounds of the Present Invention

General experimental information:

For thin liquid chromatography (TLC) monitoring of reactions, a methanol/benzene/$NH_3$(aq) 75:20:5 system was used. The products were recrystallized in acetone or chloroform/methanol (50:50 or 75:25). NMR data are given below as $^1H$ NMR ($\delta$, ppm), unless otherwise provided.

JA 1 ($C_{23}H_{22}FN_3O_3S$):

Prepared essentially as JA 2 (vide infra), although an excess of benzenesulfonyl chloride was used instead of 4-toluenesulfonyl chloride (TsCl). JA 1 was obtained as a white powder in a yield of 90%. Compound data:

Molecular Weight: 471.502; Composition: C(58.59%), H(4.70%), F(4.03%), N(8.91%), O(16.79%), S(6.80%) NMR: 14.41, 8.65, 7.86, 7.62, 7.29, 3.95, 3.33, 3.19, 3.14, 1.17, 1.00.

JA 2 ($C_{24}H_{24}FN_3O_5S$):

In a round bottomed flask, ciprofloxacin (2 g, 6.04 mmol; see U.S. Pat. No. 4,670,444) was dissolved in dimethylformamide (DMF; 30 ml) followed by addition of pyridine (1.5 ml). An excess of TsCl was added, and the reaction mixture was heated for 5 h at 98° C. The excess of TsCl was neutralized with 20% NaOH (w/v; aq), and the pH was adjusted to 7. The solvent was evaporated, and addition of cold water gave a precipitate, which was filtered and washed with cold methanol and then dried in an oven at 60° C., thereby giving JA 2 as an off-white powder (53.2% yield). Compound data;

Molecular Weight: 485.529; Composition: C(59.37%), H(4.98%), F(3.91%), N(8.65%), O(16.48%); NMR: 14.41 (s), 8.65 (s), 7.86 (d), 7.78 (d), 7.75 (d), 7.47 (m), 7.35 (m), 3.95 (m), 3.40 (m), 2.40 (m), 1.22, 1.12, 1.03, 1.17, 0.92.

JA 3 ($C_{23}H_{21}FN_4O_7S$):

Prepared in a manner essentially identical to that used for JA 2, although 4-nitrobenzenesulfonyl chloride (1.6 g, 7.22 mmol) was used instead of TsCl. JA 3 was obtained as a yellowish powder (94% yield). Compound data:

Molecular Weight: 516.5; Composition: C(53.48%), H(4.1%), F(3.68%), N(10.85%), O(21.68%), S(6.21%); NMR: 14.41, 8.65, 8.20, 7.93, 7.91, 7.86, 7.78, 7.75, 3.95, 3.40, 3.33, 3.19, 3.14, 1.22, 1.14, 1.17, 1.03, 1.00, 0.92.

JA 4 ($C_{24}H_{24}FN_3O_6S$)

Prepared essentially as JA 2, although 4-methoxybenzenesulfonyl chloride (2.3 g, 10 mmol) was used instead of TsCl. Compound data:

Molecular Weight: 501.528; Composition: C(57.48%), H(4.82%), F(3.79%), O(19.14%), S(6.39%); NMR: 14.41, 8.65, 7.86, 7.84, 7.58, 3.98, 3.84, 1.17.

JA 5 ($C_{27}H_{24}FN_3O_5S$):

Prepared essentially as JA 2, although an excess of 2-naphthalenesulfonyl chloride was used instead. JA 5 was obtained in 88% yield as a white powder. Compound data:

Molecular Weight: 521.561; Composition: C(62.18%), H(4.64%), F(4.64%), N(8.06%), O(15.34%), S(6.15%) NMR: 14.41, 8.17, 7.86, 7.78, 7.40, 3.95, 3.33, 3.19. 3.14, 1.17, 1.00.

JA 6 ($C_{26}H_{28}FN_3O_5S$)

Prepared essentially as JA 2, although an excess of mesitylsulfonyl chloride was used instead of TsCl. JA 6 was obtained as an off-white powder (85% yield). Compound data:

Molecular Weight: 513.582; Composition: C(60.80%), H(5.5%), F(3.7%), N(88.18%), O(15.58%), S(6.24%); NMR: 14.41, 8.65, 7.86, 7.84, 7.78, 6.68, 3.96, 1.01.

JA 7 ($C_{20}H_{24}FN_3O_5S$)

Prepared essentially as JA 2, but 1-propanesulfonyl chloride (5.64 ml, 50.3 mmol) was used instead of TsCl. JA 7 was obtained as a white powder (90% yield). Compound data:

Molecular Weight: 437.486; Composition: C(54.91%), H(5.53%), F(4.34%), N(9.6%), O(18.29%), S(7.33); NMR: 14.40, 8.65, 7.86, 7.78, 3.95, 3.10, 2.59, 1.96, 1.00, 0.99, 0.96.

JA 9 ($C_{24}H_{24}FN_3O_5S$):

Prepared essentially as JA 2, although phenylmethanesulfonyl chloride (1.4 g) was used instead of TsCl. JA 9 was obtained as an off-white powder (90% yield). Compound data:

Molecular Weight: 485.529; Composition: C(59.37%), H(4.98%), F(3.91%), N(8.65%), O(16.48%), S(6.6%); NMR: 14.41, 8.65, 7.78, 7.86, 7.50, 7.30, 7.17, 4.17, 3.95, 3.20, 3.12, 1.17, 1.00.

JA 10 ($C_{18}H_{20}FN_3O_5S$):

Prepared essentially as JA 2. An excess of methanesulfonyl chloride was used instead of TsCl. JA 10 was obtained in 95% yield as a creamy powder. Compound data:

Molecular Weight: 409.433; Composition: C(52.80%), H(4.92%), F(4.64%), N(10.26%), O(19.54%), S(7.83%); NMR: 14.41, 8.65, 7.86, 7.78, 3.95, 3.13, 2.93, 1.17, 1.00.

JA 12 ($C_{18}H_{17}F_4N_3O_5S$)

Prepared essentially as JA 2, although an excess of trifluoromethanesulfonyl chloride was used instead of TsCl. The required reaction time was 45 min in DMF. JA 12 was obtained as a white powder. Compound data:

Molecular Weight: 463.404; Composition: C(46.65%), H(3.7%), F(16.4%), N(9.07%), O(17.26%), S(6.92%); NMR: 14.41, 8.65, 7.86, 7.78, 3.95, 3.32, 3.19, 3.14, 1.17, 1.00.

JA 13 ($C_{21}H_{19}BrFN_3O_5S_2$):

Prepared essentially as JA 2, although 5-bromothiophene-2-sulfonyl chloride (1.6 g) was used instead of TsCl. The yield of JA 13 was 88%. Compound data:

Molecular Weight: 556.427; Composition: C(45.33%), H(3.44%), Br(14.36%), F(3.41%), N(7.55%), O(14.38%), S(11.53%); NMR: 14.41, 7.86, 7.78, 7.03, 6.89, 3.95, 3.20, 1.17, 1.00.

JA 14 ($C_{23}H_{20}Cl_2FN_3O_6S$)

Prepared essentially as JA 2, although an excess of 3,5-dichloro-2-hydroxybenzenesulfonyl chloride was used instead of TsCl and the reaction required 24 h for completion. The yield of JA 14 was 63%. Compound data:

Molecular Weight: 556.391; Composition: C(49.65%), H(3.62%), Cl(12.74%), F(3.41%), N(7.55%), O(17.25%), S(5.76%); NMR: 10.69, 8.65, 7.98, 7.86, 7.78, 3.95, 3.33, 3.40, 3.19, 3.14, 1.17, 1.03, 1.00.

JA 20 ($C_{22}H_{21}FN_4O_7S$):

Prepared essentially as JA 2, although norfloxacin (2 g, 6.3 mmol; see U.S. Pat. No. 4,146,719) was used instead of ciprofloxacin and 4-nitrobenzenesulfonyl chloride (1.7 g) was used instead of TsCl as an electrophilic reagent. JA 20 was obtained in 81% yield as a creamy powder. Compound data:

Molecular Weight: 504.489; Composition: C(52.38%), H(4.20%), F(3.77%), N(11.11%), O(22.20%), S(6.36%); NMR: 14.41, 8.93, 8.20, 7.93, 7.81, 7.43, 4.55, 3.40, 3.33; 3.19, 3.14, 1.40.

JA 21 ($C_{23}H_{24}FN_3O_6S$)

Prepared essentially as JA 20, although the electrophilic reagent used was 4-methoxybenzenesulfonyl chloride (2 g, 9.7 mmol). JA 21 was obtained as an off-white powder (96% yield). Compound data:

Molecular Weight: 489.518; Composition: C(56.43%), H(4.94%), F(3.88%), N(8.58%), O(19.61%), S(6.55%); NMR: 14.41, 8.93, 7.81, 7.56, 7.43, 6.85, 4.55, 3.84, 3.40, 3.33, 3.19, 3.14, 1.40.

JA 26 ($C_{23}H_{24}FN_3O_5S$):

Prepared essentially as JA 20, although the electrophilic reagent used was phenylmethanesulfonyl chloride (1.8 g). JA 26 was obtained as a creamy powder (84% yield). Compound data:

Molecular Weight: 473.518; Composition: C(58.34%), H(5.11%), F(4.01%), N(8.87%), O(16.89%), S(6.77%); NMR: 14.41, 8.93, 7.81, 7.43, 7.31, 7.17, 4.55, 4.17, 3.20, 3.12, 1.40.

JA 31 ($C_{23}H_{20}Cl_2FN_3O_6S$)

Prepared essentially as JA 20, although the electrophilic reagent used was 3,5-dichloro-2-hydroxybenzenesulfonyl chloride (2.5 g, 9.6 mmol). JA 31 was obtained as a creamy powder (75% yield). Compound data:

Molecular Weight: 544.381; Composition: C(48.54%), H(3.70%), Cl(13.02%), F(3.49%), N(7.72%), O(17.63%), S(5.89%); NMR: 10.69; 8.93, 7.98, 7.81, 7.43, 4.55, 3.40, 3.33, 3.19, 3.14, 1.40.

JA 39 ($C_{21}H_{19}ClFN_5O_3$)

2,6-dichloropyrazine (1 g, 6.7 mmol) was reacted with ciprofloxacin (2 g, 6 mmol) using DMF (40 ml) as solvent in the presence of pyridine (1.5 ml). The reaction mixture was refluxed at 123° C. for 5 h. Then ice water was added, and the precipitated powder product was washed with methanol and dried. In an alternative approach, the DMF was removed in vacuo using a rotary evaporator, followed by addition of ice water (50 ml). The obtained precipitate was washed with cold water and methanol up to a point where no yellowish filtrate was observed. JA 39 was obtained as a brown powder (90% yield). Compound data:

Molecular Weight: 443.859; Composition: C(S6.83%), H(4.31%), Cl(7.99%), F(4.28%), N(15.78%), O(10.81%); NMR: 14.41, 8.65, 8.06, 7.78, 7.54, 3.95, 3.84, 3.32, 3.27, 1.17, 1.00.

JA 40 ($C_{22}H_{20}BrFN_4O_3$):

Prepared essentially as JA 39, but 2,5-dibromopyridine (1.43 g, 6.04 mmol) was used instead of 2,6-dichloropyrazine. JA 40 was obtained in 77% yield. Compound data:

Molecular Weight: 487.322; Composition: C(54.22%), H(4.14%), Br(16.40%), F(3.90%), N(11.50%), O(9.85%); NMR: 14.41, 8.65, 8.09, 7.78, 7.54, 7.24, 6.43, 3.95, 3.84, 3.32, 3.27, 1.17, 1.00.

JA 42 ($C_{22}H_{20}ClFN_4O_3$)

Prepared essentially as JA 39, although 2,6-dichloropyridine (0.9 g, 6.04 mmol) was used instead of 2,6-dichloropyrazine and the reaction temperature was 120° C. JA 42 was obtained as a white powder (91% yield). Compound data:

Molecular Weight:.442.870; Composition: C(S9.66%), H(4.55%), Cl(8.01%), F(4.29%), N(12.65%), O(10.84%);

NMR: 14.41, 8.65, 7.78, 7.54, 7.54, 7.46, 7.01, 6.40, 3.95, 3.84, 3.32, 3.27, 1.17, 1.00.

JA 43 ($C_{21}H_{19}ClFN_3O_5S_2$):

Prepared essentially as JA 2, but 5-chlorothiophene-2-sulfonylchloride (1.31 g, 6.03 mmol) was used instead of TsCl. The reaction temperature was 110° C. and JA 43 was obtained as a white powder (77.6% yield). Compound data:

Molecular Weight: 511.976; Composition: C(49.26%), H(3.74%), Cl(6.92%), F(3.71%), N(8.21%), O(15.63%), S(12.53%) NMR: 14.41, 8.65, 7.86, 7.78, 6.95, 6.82, 3.95, 3.20, 1.17, 1.00.

JA 46 ($C_{21}H_{20}FN_5O_3$)

Prepared essentially as JA 39, although 2-chloropyrazine was used as electrophilic agent. JA 46 was obtained in 80% yield as a white powder. Compound data:

Molecular Weight: 409.414; Composition: C(61.61%), H(4.92%), F(4.64%), N(17.11), O(11.72%) NMR: 14.41, 8.65, 8.08, 7.84, 7.78, 7.54, 3.95, 3.84, 3.32, 3.27, 1.17, 1.00

JA 61 ($C_{18}H_{13}BrFN_3O_3$):

Prepared essentially as JA 68 (vide infra), although 2 g of IM was used, and the nucleophilic reagent was 2-amino-5-bromopyridine (7 g). JA 61 was obtained as a creamy powder (86% yield). Compound data:

Molecular Weight; 418.217; Composition: C(51.69%), H(3.13%), Br(19.11%), F(4.54%), N(10.05%), O(11.48%); NMR: 12.3, 8.65, 8.40, 8.18, 7.55, 7.15, 6.71, 4.11, 1.17, 1.00.

JA 68 ($C_{19}H_{16}FN_3O_3$):

7-chloro-1-cyclopropyl-6-fluoro-4-oxo-1,4-dihydro-3-quinolinecarboxylic acid (4 g, 14.2 mmol; hereinafter denoted "IM") and 4-picolylamine (8 g) as nucleophilic reagent were refluxed overnight in DMF (50 ml) and pyridine (3 ml). After completion of the reaction, the solvents were evaporated and cold water was added, whereby a precipitate was obtained. The precipitate was washed with water followed by methanol, after which it was filtered and dried. JA 68 was obtained as a pale yellowish powder (73% yield) which was recrystallized from chloroform/acetone 70:30. A TLC spot of JA 68 displays fluorescence when exposed to UV light. Compound data:

Molecular Weight: 353.347;

Composition: C(64.58%), H(4.56%), F(S.38%), N(11.89%), O(13.58%); NMR: 11.77, 8.70, 8.65, 8.08, 7.48, 6.41, 4.33, 4.11, 1.17, 1.00.

IM ($C_{13}H_9ClFNO_3$) was prepared as follows:

Condensation of 2,4-dichloro-5-fluoroacetophenone 2 with diethyl carbonate in the presence of NaH yielded ethyl 2,4-dichloro-5-fluorobenzoylacetate 3. Treatment of the latter with triethyl orthoformate in acetic anhydride gave the carbon homologue enol ether intermediate 4 which was allowed to react with a slight excess of cyclopropylamine in methylene chloride at room temperature to give the enaminoketoester 5. Cyclization of the latter with 1 molar equivalent of NaH in refluxing dioxane yielded ethyl 1,4-dihydro-4-oxo-quinoline-3-carboxylate 6 which was then hydrolysed with aqueous NaOH to give 1-cyclopropyl-6-chloro-7-fluoro-1,4-dihydro-4-oxo-quinoline-3-carboxylic acid (IM) 7. See also Scheme 1 below (Maurer, F. and Grohe, K., DE 3 435 392 through Chem. Abst., Vol. 105, No.5, 1984, pp. 97158e). Compound data:

Molecular Weight: 281.667; Composition: C(55.43%), H(3.22%), Cl(12.59%), F(6.74%), N(4.97%), O(17.04%); NMR (δ ppm; relative intensity): 14.41;0.13, 8.65;6.37, 8.22;1.62, 4.11;2.3, 1.22;0.06, 1.12;0.14, 1.03;0.14, 1.17;0.91, 1.00;0.90, 0.92;0.06.

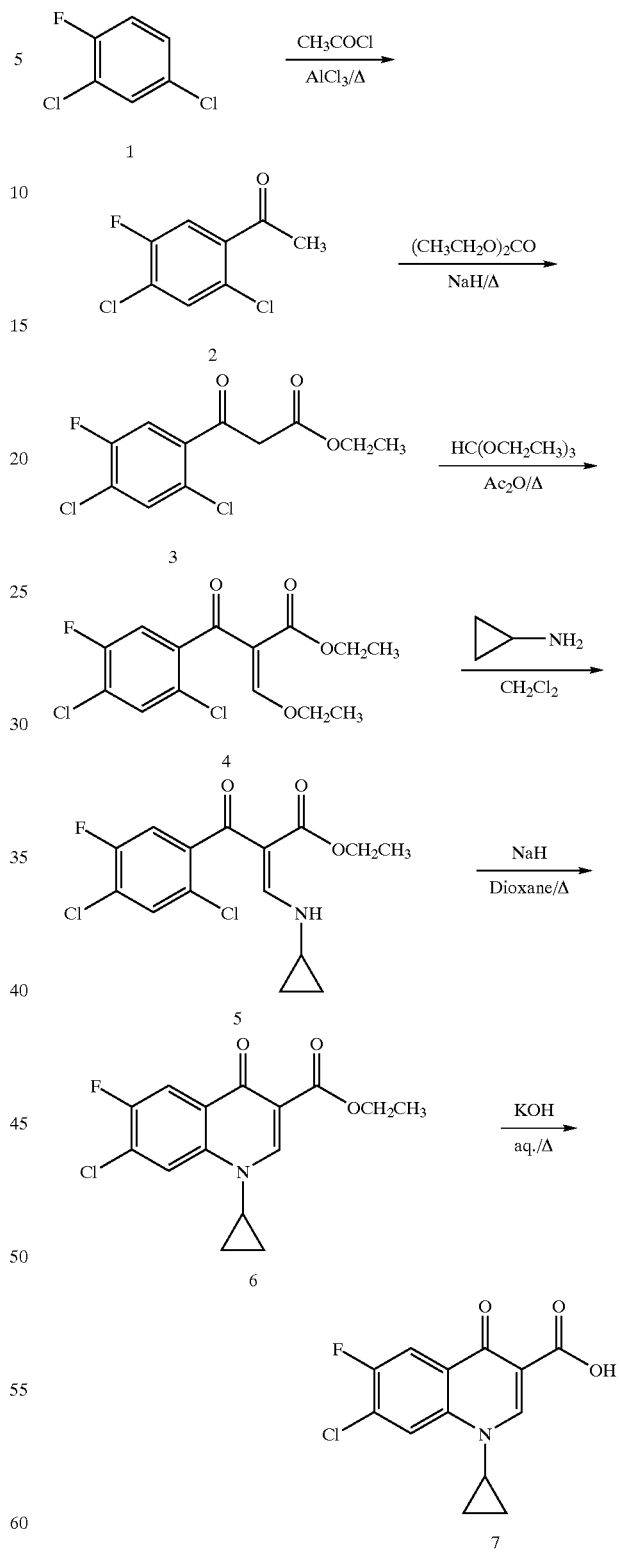

Scheme 1

JA 69 ($C_{20}H_{21}FN_2O_5$)

Prepared essentially as JA 68 (vide supra), although 2 g of IM was used, and the nucleophilic reagent was 4-aminocyclohexanecarboxylic acid (7 g). JA 69 was obtained as a white powder (86% yield). Compound data:

Molecular Weight: 388.390; Composition: C(61.85%), H(5.45%), F(4.89%), N(7.21%), O(20.60%); NMR: 10.34, 8.65, 8.01, 6.31, 4.11, 3.29, 2.75, 2.10, 1.77, 1.59, 1.17, 1.00.

JA 70 ($C_{21}H_{17}FN_2O_5$)

Prepared essentially as JA 68, although the amount of IM used was 5.11 g and the nucleophilic reagent was 4-(aminomethyl)benzoic acid (6 g). The reaction temperature was 125° C. for 4 h, and JA 70 was obtained as a creamy powder (61.2% yield). Compound data:

Molecular Weight: 396.369; Composition: C(63.63%), H(4.32%), F(4.79%), N(7.07%), O(20.18%); NMR: 12.13, 8.65, 8.08, 7.87, 7.48, 6.41, 4.48, 4.11, 1.17, 1.00.

JA 73 ($C_{18}H_{19}FN_2O_4$):

Prepared essentially as JA 68, although the amount of IM used was 8 g, the nucleophilic reagent was tetrahydrofurylamine (12.00 g), and the reaction temperature was 120° C. for 3 h. JA 73 was obtained as a white powder (75% yield). Compound data:

Molecular Weight: 346.353; NMR: 10.27, 8.65, 8.06,. 6.38, 4.11, 3.89, 3.84, 2.98, 2.77, 1.11, 1.17, 1.00.

JA 74 ($C_2OH_{21}FN_2O_5$):

Prepared essentially as JA 68, although 2 g of IM was used, and the nucleophilic reagent was 4-isopropylaniline (2 g). JA 69 was obtained as a white powder (86% yield). Compound data:

Molecular Weight: 380.412; Composition: C(69.46%), H(5.56%), F(4.99%), N(7.36%), O(12.62%); NMR: 12.22, 8.65, 8.18, 7.20, 7.05, 4.11, 3.03, 1.15, 1.20, 1.00.

JA 76 ($C_{20}H_{24}FN_3O_3$):

Prepared essentially as JA 68, although 2 g of IM was used, and the nucleophilic reagent was 2-(1-piperidinyl)-1-ethanamine (6 g). JA 76 was obtained as a white powder (86% yield). Compound data:

Molecular Weight: 373.421; Composition: C(64.33%), H(6.48%), F(5.09%), N(11.25%), O(12.85%); NMR: 10.30, 8.65, 7.94, 6.34, 4.11, 3.21, 2.80, 2.47, 2.40, 1.58, 1.48, 1.17, 1.03, 1.00.

JA 91 ($C_{25}H_{20}FN_3O_5S$):

Prepared exactly as JA 2 (vide supra), although instead JA 68 (0.8 g, 2.27 mmol) was reacted with benzenesulfonyl chloride (3 g). JA 91 was obtained in 52% yield. Compound data:

Molecular Weight: 493.508; Composition: C(60.84%), H(4.08%), F(3.85%), O(16.21%), S(6.50%); NMR: 14.41, 9.01, 8.65, 8.27, 7.81, 7.67, 7.42, 7.08, 4.64, 4.11, 1.17, 1.00.

JA 103 ($C_{16}H_{18}FN_3O_3$):

Prepared essentially as JA 68, although 3 g of IM was used, and the nucleophilic reagent was ethylenediamine (3.5 g). When the reaction was complete, the solvent was removed in vacuo and acetone (30 ml) was added to the residue. It should be noted that methanol should not be used at all here. An excess of cold water was subsequently added to obtain JA 103 as a suspended powder, which was filtered, dried and recrystallized. JA 103 was obtained as a white powder (84% yield). Compound data:

Molecular Weight: 319.331; Composition: C(60.18%), H(5.68%), F(5.95%), N(13.16%), O(15.03%); NMR: 8.65, 7.97, 6.26, 6.12, 4.11, 3.31, 2.26, 1.17, 1.00.

JA 105 ($C_{19}H_{22}FN_3O_3$):

Prepared exactly as JA 103, although 3 g of IM was used, and the nucleophilic reagent was 1,2-diaminocyclohexane (6 g). JA 105 was obtained as a brownish powder (81% yield). Compound data:

Molecular Weight: 359.395; Composition: C(63.50%), H(6.17%), P(5.29%), N(11.69%), O(13.36%); NMR: 8.65, 8.01, 6.31, 5.32, 4.11, 2.83, 2.58, 1.92, 1.46, 1.17, 1.00.

JA 117 ($C_{24}H_{22}FN_3O_8S$):

Prepared essentially as JA 2 (vide supra), although instead 4-nitrobenzenesulfonyl chloride (0.8 g) was used as electrophile. JA 117 was obtained as a white powder (76% yield). Compound data:

Molecular Weight: 531.511; Composition: C(54.23%), H(4.17%), F(3.57%), N(7.91%), O(24.08%), S(6.03%); NMR: 14.41, 8.65, 8.31, 8.12, 7.05, 4.11, 3.89, 3.75, 3.67, 1.17, 1.00.

JA 135 ($C_{25}H_{25}FN_2O_7S$):

Prepared essentially as JA 2, although 1-cyclopropyl-6-fluoro-4-oxo-7-[(tetrahydro-2-furanylmethyl)amino]-1,4-dihydro-3-quinolinecarboxylic acid and an excess of 4-methoxybenzenesulfonyl chloride were used instead. JA 135 was obtained in 86% yield as a white powder. Compound data:

Molecular Weight: 516.540; Composition: C(58.13%), H(4.68%), F(3.68%), N(5.42%), O(21.68%), S(6.21%); NMR: 14.41, 8.65, 8.24, 7.75, 7.05, 6.96, 4.11, 3.84, 3.89, 3.75, 3.67, 1.17, 1.00.

JA 136 ($C_{28}H_{25}FN_2O_6S$):

Prepared essentially as JA 2, although 1-cyclopropyl-6-fluoro-4-oxo-7-[(tetrahydro-2-furanylmethyl)amino]-1,4-dihydro-3-quinolinecarboxylic acid and an excess of 2-naphthalenesulfonyl chloride were used instead. JA 136 was obtained in 86% yield as a white powder. Compound data:

Molecular Weight: 536.572; Composition: C(62.68%), H(4.70%), F(3.54%), N(5.22%), O(17.89%), S(5.98%); NMR: 14.41, 8.65, 8.24, 8.00, 7.76, 7.40, 7.05, 4.11, 3.89, 3.67, 3.75, 1.17, 1.00.

JA 137 ($C_{26}H_{27}FN_2O_6S$):

Prepared essentially as JA 2, although 1-cyclopropyl-6-fluoro-4-oxo-7-[(tetrahydro-2-furanylmethyl)amino]-1,4-dihydro-3-quinolinecarboxylic acid and an excess of 2-phenyl-1-ethanesulfonyl chloride were used instead. JA 137 was obtained in 86% yield as a white powder. Compound data:

Molecular Weight: 514.567; Composition: C(60.69%), H(5.29%), F(3.69%), N(5.44%), O(18.66%), S(6.23%); NMR: 14.41, 8.65, 8.17, 7.39, 7.30, 6.92, 4.11, 3.79, 3.68, 2.85, 1.17, 1.00.

JA 138 ($C_{19}H_{18}F_4N_2O_6S$):

Prepared essentially as JA 144 (vide infra), although trifluoromethanesulfonyl chloride (0.6 g) was used as electrophile. JA 138 was obtained as a creamy powder (70% yield). Compound data:

Molecular Weight: 478.416; Composition: C(47.70%), H(3.79%), F(15.88%), N(5.88%), N(5.86%), O(20.07%), S(6.70%); NMR: 14.41, 8.65, 8.07, 7.31, 4.11, 3.99, 3.75, 3.61, 1.17, 1.00.

JA 139 ($C_{24}H_{23}FN_2O_6S$)

Prepared essentially as JA 117, although benzenesulfonyl chloride (0.7 g) was used as electrophile. JA 139 was obtained in 76% yield. Compound data;

Molecular Weight: 486.514; Composition; C(59.25%), H(4.77%), F(3.91%), N(S.76%), O(19.73%), S(6.59%); NMR: 14.41, 8.65, 8.24, 7.79, 7.42, 7.05, 4.11, 3.89, 3.75, 1.17, 1.00.

JA 141 ($C_{22}H_{20}ClFN_4O_4$):

Prepared essentially as JA 39, although 1-cyclopropyl-6-fluoro-4-oxo-7-[(tetrahydro-2-furanylmethyl)amino]-1,4-dihydro-3-quinolinecarboxylic acid (5.6 mmol) was used instead of ciprofloxacin. JA 141 was obtained in 78% yield as a brownish powder. Compound data:

Molecular Weight: 458.870; Composition: C(57.58%), H(4.39%), Cl(7.73%), F(4.14%), N(12.21%), O(13.95%); NMR: 14.41, 8.65, 8.15, 7.81, 4.57, 4.38, 4.11, 4.03, 3.89, 3.81, 1.17, 1.00.

JA 142 ($C_{23}H_{21}BrFN_3O_4$):

Prepared essentially as JA 141, although instead 2,5-dibromopyridine (2.85 g) was used as electrophile. JA 142 was obtained as a creamy powder (80% yield). Compound data:

Molecular Weight: 502.333; Composition: C(54.99%), H(4.21%), Br(15.91%), F(3.78%), N(8.37%), O(12.74%); NMR: 14.41, 8.65, 8.36, 8.18, 7.51, 6.36, 4.59, 4.41, 4.11, 4.03, 3.89, 3.81, 1.17, 1.00.

JA 143 ($C_{23}H_{21}ClFN_3O_4$):

Prepared essentially as JA 142, although 2,6-dichloropyridine (2.6 g) was used as electrophile. JA 143 was obtained as a creamy powder (72.3% yield). Compound data:

Molecular Weight: 457.882; Composition: C(60.33%), H(4.62%), Cl(7.74%), F(4.15%), N(9.18%), O(13.98%); NMR: 14.41, 8.65, 8.18, 7.72, 7.15, 6.33, 4.59, 4.41, 4.11, 4.03, 3.89, 3.81, 1.17, 1.00.

JA 144 ($C_{22}H_{23}FN_2O_6$):

JA 73 (1 g, 2.9 mmol) was dissolved in DMF (40 ml), after which acetoacetic ester (2.5 g; CAS #141979) was added. The reaction mixture was refluxed for 3 h at 125° C., followed by solvent removal in vacuo and cold water addition to precipitate the product. Subsequent filtration and recrystallization from acetone gave JA 144 as an off-white powder (55% yield). Compound data:

Molecular Weight: 430.426; Composition: C(61.39%), H(5.39%), F(4.41%), N(6.51%), O(22.30%); NMR: 14.41, 8.65, 8.16, 7.25, 4.91, 4.53, 4.11, 3.75, 3.53, 3.61, 1.9, 1.17, 1.00.

JA 145 ($C_{25}H_{26}FN_3O_4$)

Prepared essentially as JA 144, although 4-vinylpyridine (2 g) was used as electrophile. JA 145 was obtained as a yellowish to off-white powder (62% yield). Compound data:

Molecular Weight: 451.490; Composition: C(66.51%), H(5.80%), F(4.21%), N(9.31%), O(14.17%); NMR: 14.41, 8.65, 8.48, 7.89, 7.55, 7.11, 3.95, 3.81, 3.37, 3.19, 2.67, 1.18, 1.00.

JA 146 ($C_{25}H_{26}FN_3O_4$)

Prepared exactly as JA 145, although 2-vinylpyridine (2 g, 19 mmol) was used as electrophile. JA 146 was obtained as a light brown powder (66% yield). Compound data:

Molecular Weight: 451.490; Composition: C(66.51%), H(5.80%), F(44.21%), N(9.31%), O(14.17%); NMR: 14.41, 8.65, 8.5, 7.89, 7.53, 7.49, 7.25, 3.95, 3.81, 3.26, 2.83, 1.18, 1.00.

JA 156 ($C_{25}H_{19}FN_4O_7S$)

Prepared exactly as JA 91, although instead JA 68 (1 g) was reacted with 4-nitrophenylsulfonyl chloride. JA 156 was obtained in 75% yield. Compound data:

Molecular Weight: 538.505; Composition: C(55.76%), H(3.56%), F(3.53%), N(10.40%), O(20.80%), S(5.95%); NMR: 14.41, 9.01, 8.65, 8.31, 8.14, 7.67, 7.08, 4.64, 4.11, 1.17, 1.00.

JA 158 ($C_{24}H_{16}BrFN4O_7S$):

Prepared essentially as JA 2, although instead JA 61 (1 g, 2.4 mmol) was reacted with 4-nitrobenzenesulfonyl chloride (2.7 g, 12.2 mmnol). JA 158 was obtained as a creamy powder (67% yield). Compound data:

Molecular Weight: 603.375; Composition: C(47.77%), H(2.67%), Br(13.24%), F(3.15%), N(9.29%), O(18.56%), S(5.31%); NMR: 14.41, 8.65, 8.57, 8.35, 8.16, 7.73, 7.48, 6.80, 4.11, 1.17, 1.00.

JA 159 ($C_{24}H_{16}BrF_2N_3O_5S$):

Prepared essentially as JA 2, although instead JA 61 (1 g, 2.4 mmol) was reacted with 4-fluorobenzenesulfonyl chloride (2.5 g, 11.8 mmol), JA 159 was obtained in a yield of 70%. Compound data:

Molecular Weight: 576.368; Composition: C(50.01%), H(2.80%), Br(13.86%), F(6.59%), N(7.29%), O(13.88%), S(5.56%); NMR: 14.41, 8.65, 8.57, 8.49, 7.81, 7.73, 7.48, 6.80, 4.11, 1.17, 1.00.

JA 160 ($C_{19}H_{12}BrF_4N_3O_5S$)

Prepared exactly as JA 159, although instead JA 61 was reacted with trifluoromethylsulfonyl chloride. JA 160 was obtained in a yield of 68%. Compound data:

Molecular Weight: 550.279; Composition: C(41.47%), H(2.20%), Br(14.52%), F(13.81%), N(7.64%), O(14.54%), S(5.83%); NMR: 14.41, 8.65, 8.40, 7.74, 7.55, 7.06, 4.11, 1.17, 1.00.

JA 161 ($C_{28}H_{19}BrFN_3O_5S$)

Prepared exactly as JA 159, although instead JA 61 was reacted with 2-naphtalenesulfonyl chloride. JA 161 was obtained in a yield of 66%. Compound data:

Molecular Weight: 608.436; Composition: C(55.27%), H(3.15%), Br(13.13%), F(3.12%), N(6.91%), O(13.15%), S(5.27%); NMR: 14.41, 8.57, 8.65, 8.04, 7.74, 7.48, 7.40, 6.80, 4.11, 1.17, 1.00.

JA 162 ($C_{28}H_{25}FN_2O_6S$)

Prepared essentially as JA 2, although instead JA 73 (1 g, 2.9 mmol) was reacted with 2-naphtalenesulfonyl chloride (3.27 g, 14.9 mmol). JA 162 was obtained in a yield of 69%. Compound data:

Molecular Weight: 536.572; Composition: C(62.68%), H(4.70%), F(3.54%), N(5.22%), O(17.89%), S(5.98%); NMR: 14.41, 8.65, 8.24, 8.00, 7.76, 7.40, 7.05, 4.11, 3.89, 3.75, 3.67, 1.17, 1.00.

JA 163 ($C_{29}H_{22}FN_3O_5S$)

Prepared essentially as JA 2, although instead JA 68 (1 g) was reacted with 2-naphtalenesulfonyl chloride (3.2 g). JA 163 was obtained in a yield of 70%. Compound data:

Molecular Weight: 543.567; Composition: C(64.08%), H(4.08%), F(3.50%), N(7.73%), O(14.72%), S(5.90%); NMR: 14.41, 9.01, 8.65, 8.27, 8.02, 7.67, 7.08, 4.64, 4.11, 1.17, 1.00.

JA 164 ($C_{20}H_{15}F_4N_3O_5S$):

Prepared exactly as JA 163, although instead JA 68 (1 g) was reacted with trifluoromethanesulfonyl chloride (2.4 g, 14.2 mmol). JA 164 was obtained in a yield of 72%. Compound data:

Molecular Weight: 485.410; Composition: C(49.49%), H(3.11%), F(15.66%), N(8.66%), O(16.48%), S(6.61%); NMR; 14.41, 9.01, 8.65, 8.09, 7.50, 7.33, 4.59, 4.11, 1.17, 1.00.

JA 165 ($C_{24}H_{16}ClFN_4O_3$):

Prepared exactly as JA 163, although instead JA 68 (1 g) was reacted with 2,6-dichloropyridine (2 g, 13.5 mmol). JA 165 was obtained in a yield of 75%. Compound data:

Molecular Weight: 464.876; Composition: C(62.01%), H(3.90%), Cl(7.63%), F(4.09%), N(12.05%), O(10.32%); NMR: 14.41, 8.72, 8.65, 8.20, 7.74, 7.51, 7.15, 6.36, 5.56, 4.11, 1.17, 1.00.

JA 166 ($C_{23}H_{17}ClFN_5O_3$):

Prepared exactly as JA 163, although instead JA 68 (1 g, 2.83 mmol) was reacted with dichloropyrazine (0.6 g, 4.0 mnol). JA 166 was obtained in a yield of 66%. Compound data:

Molecular Weight: 465.864; Composition: C(59.30%), H(3.68%), Cl(7.61%), F(4.08%), N(15.03%), O(10.30%); NMR: 14.41, 8.72, 8.65, 8.16, 7.84, 7.60, 5.54, 4.11, 1.17, 1.00.

JA 167 ($C_{24}H_{18}BrFN_4O_3$):

Prepared exactly as JA 163, although instead JA 68 (1 g, 2.83 mmol) was reacted with 2,5-dibromopyridine. JA 167 was obtained in a yield of 69%. Compound data:

Molecular Weight: 509.327; Composition: C(56.60%), H(3.56%), Br(15.69%), F(3.73%), N(11.00%), O(9.42%); NMR: 14.41, 8.72, 8.65, 8.38, 8.20, 7.51, 6.37, 5.56, 4.11, 1.17, 1.00.

JA 168 ($C_{27}H_{20}FN_3O_9S$):

Prepared exactly as JA 2, although instead 4-nitrobenzenesulfonyl chloride (2.2 g) was used as electrophile and reacted with JA 70 (1.0 g). JA 168 was obtained as a creamy powder (72% yield). Compound data:

Molecular Weight: 581.527; Composition: C(55.77%), H(3.47%), F(3.27%), N(7.23%), O(24.76%), S(5.51%); NMR: 13.63, 8.65, 8.31, 8.14, 8.18, 7.68, 7.08, 4.67, 4.11, 1.17, 1.00.

JA 169 ($C_{31}H_{23}FN_2O_7S$):

Prepared essentially as JA 168, although instead JA 70 (1 g, 2.5 mmol) was reacted with 2-naphtalenesulfonyl chloride (2.3 g). JA 169 was obtained as a white powder (70% yield). Compound data:

Molecular Weight: 586.588; Composition: C(63.47%), H(3.95%), F(3.24%), N(4.78%), O(19.09%), S(5.47%); NMR: 13.63, 8.65, 8.18, 7.68, 7.40, 7.08, 4.67, 4.11, 1.17, 1.00.

JA 170 ($C_{22}H_{16}F_4N_2O_7S$)

Prepared exactly as JA 169, although instead trifluoromethanesulfonyl chloride was used as the electrophilic reagent. JA 170 was obtained as a white powder (70% yield). Compound data:

Molecular Weight: 528.431; Composition: C(50.00%), H(3.05%), F(14.38%), N(5.30%), O(21.19%), S(6.07%); NMR: 13.63, 8.65, 8.18, 7.51, 7.33, 4.62, 4.11, 1.17, 1.00.

JA 171 ($C_{26}H_{19}ClFN_3O_5$):

Prepared exactly as JA 169, although instead 2,6-dichloropyridine (0.45 g) was used as the electrophilic reagent. JA 171 was obtained in 68% yield. Compound data:

Molecular Weight: 507.897; Composition: C(61.48%), H(3.77%), Cl(6.98%), F(3.74%), N(8.27%), O(15.75%); NMR: 13.63, 8.65, 8.20, 7.89, 7.74, 7.53, 7.15, 6.36, 5.59, 4.11, 1.17, 1.00.

JA 172 ($C_{25}H_{18}ClFN_4O_5$):

Prepared exactly as JA 169, although instead dichloropyrazine (0.45 9) was the electrophile used. JA 172 was obtained in 70% yield. Compound data:

Molecular Weight: 508.885; Composition: C(59.00%), H(3.57%), Cl(6.97%), F(3.73%), N(11.01%), O(15.72%); NMR: 13.63, 8.65, 8.16, 7.89, 7.62, 5.56, 4.11, 1.17, 1.00.

JA 173 ($C_{26}H_{19}BrFN_3O_5$):

Prepared exactly as JA 169, although instead 2,5-dibromopyridine (1 g) was the electrophile used. JA 173 was obtained in 77% yield. Compound data:

Molecular Weight: 552.349; Composition: C(56.54%), H(3.47%), Br(14.47%), F(3.44%), N(7.61%), O(14.48%); NMR: 13.63, 8.65, 8.38, 7.89, 7.53, 6.37, 5.59, 4.11, 1.17, 1.00.

B626 ($C_{27}H_{21}F_2N_5O_5S$):

In a round bottomed flask, 6-fluoro-1-(4-fluorophenyl)-4-oxo-7-(1-piperazinyl)-1,4-dihydro-3-quinolinecarboxylic acid (5.56 mmol) was dissolved in a 10% aqueous solution of KOH (7.5 ml), followed by addition of distilled water (10 ml) in order to obtain a clear solution. A solution of 4-nitrophenylisothiocyanate (1.02 g, 5.56 mmol) in acetone (30 ml) was then added to the clear solution. The reaction mixture was refluxed for 0.5 h, after which distilled water was added and the pH was adjusted to 7 by using HCl (2N). The resulting precipitate was filtered off, washed with water and recrystallized from chloroform/acetone 70:30. The yield of B626 was 91%. Compound data:

Molecular Weight: 565.549; Composition: C(57.34%), H(3.74%), F(6.72%), N(12.38%), O(14.15%), S(5.67%); NMR: 12.11, 8.74, 8.04, 7.95, 7.63, 7.16, 6.91, 6.73, 3.34, 3.35, 2.56, 2.60.

B627 ($C_{24}H_{21}ClFN_5O_5S$):

Prepared exactly as B626, although 7-(3-amino-1-pyrrolidinyl)-8-chloro-1-cyclopropyl-6-fluoro-4-oxo-1,4-dihydro-3-quinolinecarboxylic acid (5.56 mmol) was used instead. The yield of B627 was 96%. Compound data:

Molecular Weight: 545.971; Composition: C(52.80%), H(3.88%), Cl(6.49%), F(3.48%), N(12.83%), O(14.65%), S(5.87%); NMR: 10.29, 8.71, 8.16, 8.09, 6.97, 5.27, 3.99, 3.78, 3.66, 3.26, 2.00, 1.97, 1.53, 1.17, 1.03, 1.00.

B628 ($C_{23}H_{20}F_3N_5O_5S$):

Prepared exactly as B626, although 6,8-difluoro-1-(2-fluoroethyl)-4-oxo-7-(1-piperazinyl)-1,4-dihydro-3-quinolinecarboxylic acid (5.56 mmol) was used instead. The yield of B628 was 90%. Compound data:

Molecular Weight: 535.497; Composition: C(51.59%), H(3.76%), F(10.64%), N(13.08%), O(14.94%), S(5.99%); NMR: 12.04, 8.65, 8.04, 7.13, 6.92, 4.11, 3.7, 3.63, 3.39, 3.29, 2.70, 2.62, 2.09, 1.18, 1.00.

B629 ($C_{26}H_{26}FN_5O_5S$):

Prepared exactly as B626, although 1-cyclopropyl-6-fluoro-5-methyl-7-(3-methyl-1-piperazinyl)-4-oxo-1,4-dihydro-3-quinolinecarboxylic acid (5.56 mmol) was used instead. The yield of B629 was 91%. Compound data:

Molecular Weight: 539.580; Composition: C(57.87%), H(4.86%), F(3.52%), N(12.98%), O(14.83%), S(5.94%); NMR: 12.04, 8.65, 8.04, 7.13, 6.92, 4.11, 3.70, 3.63, 3.39, 3.29, 2.70, 2.62, 2.09, 1.18, 1.00.

B630 ($C_{24}H_{23}F_2N_5O_5S$):

Prepared exactly as B626, although 1-ethyl-6,8-difluoro-7-(3-methyl-1-piperazinyl)-4-oxo-1,4-dihydro-3-quinolinecarboxylic acid.HCl (2 g, 5.15 mmol) was used instead. The yield of B630 was 93%. Compound data:

Molecular Weight: 531.533; Composition: C(54.23%), H(4.36%), F(7.15%), N(13.18%), O(15.05%), S(6.03%); NMR: 12.04, 9.02, 8.04, 7.85, 6.92, 4.51, 3.66, 3.50, 3.43, 2.70, 2.60, 1.55, 1.19.

B631 ($C_{24}H_{22}FN_5O_6S$):

Prepared exactly as B626, although 9-fluoro-3-methyl-7-oxo-10-(1-piperazinyl)-2,3-dihydro-7H-[1,4]oxazino[2,3,4-ij]quinoline-6-carboxylic acid (5.56 mmol) was used instead. The yield of B631 was 92%. Compound data:

Molecular Weight: 527.526; Composition: C(54.64%), H(4.20%), F(3.60%), N(13.28%), O(18.20%), S(6.08%); NMR: 12.11, 8.93, 8.04, 7.35, 6.91, 4.52, 4.49, 4.42, 3.43, 3.24, 2.95, 2.56, 2.60.

B632 ($C_{23}H_{20}FN_5O_5S_2$):

Prepared exactly as B626, although 9-fluoro-7-oxo--(1-piperazinyl)-2,3-dihydro-7H-[1,4]thiazino[2,3,4-ij]quinoline-6-carboxylic acid (5.56 mmol) was used instead. The yield of B632 was 96%. Compound data:

Molecular Weight: 529.566; Composition: C(52.16%), H(3.81%), F(3.59%), N(13.22%), O(15.11%), S(12.11%); NMR: 12.11, 8.93, 8.04, 7.35, 6.91, 4.52, 4.49, 4.42, 3.43, 3.24, 2.95, 2.56, 2.60.

B633 ($C_{24}H_{22}F_2N_6O_5S$)

Prepared exactly as B626, although 5-amino-1-cyclopropyl-6,8-difluoro-4-oxo-7-(1-piperazinyl)-1,4-dihydro-3-quinolinecarboxylic acid (5.56 mmol) having its 5-amino group acetyl-protected (by previous reaction with Ac$_2$O) was used instead. The yield of B633 was 96%. Compound data:

Molecular Weight: 544.532; Composition: C(52.94%), H(4.07%), F(6.98%), N(15.43%), O(14.69%), S(5.89%); NMR: 11.07, 8.84, 8.04, 6.91, 4.26, 3.55, 3.49, 2.60, 2.56, 1.17, 1.00.

B634 ($C_{28}H_{22}F_3N_5O_5S$):
Prepared exactly as B626, although 1-(2,4-difluorophenyl)-6-fluoro-7-(3-methyl-1-piperazinyl)-4-oxo-1,4-dihydro-3-quinolinecarboxylic acid (5.56 mmol) was used instead. The yield of B634 was 98%. Compound data:
Molecular Weight: 597.566; Composition: C(56.28%), H(3.71%), F(9.54%), N(11.72%), O(13.39%), S(5.37%); NMR: 12.04, 8.93, 8.04, 7.59, 7.08, 6.92, 6.79, 6.59, 3.69, 3.39, 3.32, 2.70, 2.60, 1.19.

B635 ($C_{34}H_{25}F_3N_6O_9S_2$):
Prepared exactly as JA 2, although 1-(2,4-difluorophenyl)-6-fluoro-7-{3-methyl-4-[(4-nitroanilino)carbothioyl]-1-piperazinyl}-4-oxo-1,4-dihydro-3-quinolinecarboxylic acid was reacted with 4-nitrobenzenesulfonyl chloride instead of TsCl. B635 was obtained as a creamy powder (92% yield). Compound data:
Molecular Weight: 782.725; Composition: C(52.17%), H(3.22%), F(7.28%), N(10.74%), O(18.40%), S(8.19%); NMR: 14.41, 8.93, 8.26, 7.64, 7.57, 7.09, 6.79, 6.59, 3.53, 3.41, 3.23, 3.11, 2.49, 1.22.

B636 ($C_{24}H_{24}F_2N_4O_3S$)
Prepared essentially as B626, although 1-ethyl-6,8-difluoro-7-(3-methyl-1-piperazinyl)-4-oxo-1,4-dihydro-3-quinolinecarboxylic acid.HCl (2.6 mmol) was instead reacted with phenylisothiocyanate (3 mmol). B636 was obtained in 91% yield as a white powder. Compound data:
Molecular Weight: 486.535; Composition: C(59.25%), H(4.97%), F(7.81%), N(11.52%), O(9.87%), S(6.59%); NMR: 12.04, 9.02, 7.85, 7.61, 7.22, 4.51, 3.66, 3.63, 3.50, 3.43, 3.24, 2.70, 2.61, 1.55, 1.19.

B637 ($C_{24}H_{22}F_2N_4O_3S$):
Prepared exactly as B626, although 4-fluorophenylisothiocyanate was used instead of 4-nitrophenylisothiocyanate. B637 was obtained in 91% yield as a white powder. Compound data:
Molecular Weight: 484.519; Composition: C(59.49%), H(4.58%), F(7.84%), N(11.56%), O(9.91%), S(6.62%); NMR: 12.11, 8.65, 7.78, 7.70, 7.57, 7.14, 3.95, 3.43, 3.35, 2.56, 2.6, 1.17, 1.00.

B638 ($C_{23}H_{22}FN_5O_5S$):
Prepared exactly as B626, although 1-ethyl-6-fluoro-4-oxo-7-(1-piperazinyl)-1,4-dihydro-3-quinolinecarboxylic acid (5.56 mmol) was used instead. The yield of B638 was 93%. Compound data:
Molecular Weight: 499.516; Composition: C(55.30%), H(4.44%), F(3.80%), N(14.02%), O(16.01%), S(6.42%); NMR: 12.11, 8.93, 8.04, 7.81, 7.15, 6.91, 4.55, 3.43, 3.37, 2.60, 2.56, 1.40.

JA 1000 ($C_{28}M_{18}F_4N_4O_5S$)
Prepared essentially as JA 2, although 7-[(1R,5S)-6-amino-3-azabicyclo[3.1.0]hex-3-yl]-1-(2,4-difluorophenyl)-6-fluoro-4-oxo-1,4-dihydro[1,8]naphthyridine-3-carboxylic acid (6.3 mmol; see U.S. Pat. No. 5,164,402) and 4-fluorobenzenesulfonyl chloride (7 mmol) were used instead. JA 1000 was obtained in 82% yield as a creamy powder. Compound data:
Molecular Weight: 574.505; Composition: C(54.36%), H(3.16%), F(13.23%), N(9.75%), O(13.92%), S(5.58%); NMR: 9.36, 8.88, 8.44, 7.64, 7.30, 6.92, 6.72, 3.00, 2.80, 2.66, 0.96.

JA 1001 ($C_{25}H_{17}ClF_3N_5O_3$):
Prepared essentially as JA 42, although 7-[(1R,5S)-6-amino-3-azabicyclo[3.1.0]hex-3-yl]-1-(2,4-difluorophenyl)-6-fluoro-4-oxo-1,4-dihydro[1,8]naphthyridine-3-carboxylic acid (6.3 mmol) was used instead of ciprofloxacin. JA 1001 was obtained in 90% yield as a creamy powder. Compound data:
Molecular Weight: 527.882; Composition: C(56.88%), H(3.25%), Cl(6.72%), F(10.80%), N(13.27%), O(9.09%); NMR: 8.88, 8.77, 8.44, 7.54, 7.08, 6.92, 6.72, 6.30, 3.19, 2.85, 2.51, 1.14.

JA 1002 ($c_{24}H_{16}ClF_3N_6O_3$):
Prepared essentially as JA 39, although 7-[(1R,5S)-6-amino-3-azabicyclo[3.1.0]hex-3-yl]-1-(2,4-difluorophenl)-6-fluoro-4-oxo-1,4-dihydro[1,8]naphthyridine-3-carboxylic acid (6.3 mmol) was used instead of ciprofloxacin. JA 1002 was obtained in 90% yield as a brownish powder. Compound data:
Molecular Weight: 528.870; Composition: C(54.50%), H(3.05%), Cl(6.70%), F(10.78%), N(15.89%), O(9.08%); NMR: 9.44, 8.88, 8.44, 8.08, 7.82, 7.27, 6.92, 6.72, 3.19, 2.72, 1.14.

JA 1003 ($C_{27}H_{19}F_4N_6O_4$):
Prepared exactly as B626, although 7-[(1R,5S)-6-amino-3-azabicyclo[3.1.0]hex-3-yl]-1-(2,4-difluorophenyl)-6-fluoro-4-oxo-1,4-dihydro[1,8]naphthyridine-3-carboxylic acid (5.6 mmol) and 4-fluorophenylthiocyanate (5.6 mmol) were used instead. JA 1003 was obtained in 90% yield as a creamy powder. Compound data:
Molecular Weight: 527.882; Composition: C(58.59%), H(3.46%), F(13.73%), N(12.65%), O(11.56%); NMR: 9.06, 8.88, 8.44, 7.27, 7.06, 6.96, 6.72, 3.08, 2.75, 1.64, 1.42.

JA 1004 ($C_{27}H_{19}F_4N_5O_3S$):
Prepared exactly as JA 1003, although 4-fluorophenylisothiocyanate (5.6 mmol) was used instead of 4-fluorophenylthiocyanate. JA 1003 was obtained in 90% yield as a creamy powder. Compound data:
Molecular Weight: 569.531; Composition: C(56.94%), H(3.36%), F(13.34%), N(12.30%), O(8.43%), S(5.63%); NMR: 9.73, 8.88, 8.44, 7.81, 7.27, 7.19, 6.92, 6.72, 3.08, 2.73, 1.91, 1.48.

JA 1005 ($C_{39}H_{25}F_4N_7O_{11}S_3$):
Prepared essentially as JA 2, although 1-(2,4-difluorophenyl)-6-fluoro-7-((1R,5S)-6-{[(4-fluoroanilino)carbothioyl]amino}-3-azabicyclo[3.1.0]hex-3-yl)-4-oxo-1,4-dihydro[1,8]naphthyridine-3-carboxylic acid (6.3 mmol; see U.S. Pat. No. 5,164,402) and an excess of 4-fluorobenzenesulfonyl chloride were used instead. JA 1005 was obtained in 79% yield as a creamy powder. Compound data:
Molecular Weight: 939.848; Composition: C(49.84%), H(2.68%), F(8.09%), N(10.43%), O(18.73%), S(10.24%); NMR: 14.41, 8.88, 8.44, 8.35, 7.49, 7.27, 6.92, 6.72, 3.06, 2.76, 1.66.

JA 1006 ($C_{26}H_{26}F_2N_4O_8S$):
Prepared exactly as JA 1005, although 7-[3-(aminomethyl)-3-(fluoromethyl)-1-pyrrolidinyl]-1-cyclopropyl-6-fluoro-8-methoxy-4-oxo-1,4-dihydro-3-quinolinecarboxylic acid (6 mmol; see U.S. Pat. No. 5,677,316) was used instead. JA 1006 was obtained in 72% yield as a creamy powder. Compound data:
Molecular Weight: 592.570; Composition: C(52.70%), H(4.42%), F(6.41%), N(9.45%), O(21.60%), S(5.41%); NMR: 10.06, 8.61, 8.41, 7.83, 4.22, 4.09, 4.02, 3.61, 3.45, 3.27, 2.90, 2.79, 2.69, 1.89, 1.83, 1.18, 1.00, 0.92.

JA 1007 ($C_{24}H_{24}ClF_2N_6O_4$):
Prepared essentially as JA 39, although 7-[3-(aminomethyl)-3-(fluoromethyl)-1-pyrrolidinyl]-1-cyclopropyl-6-fluoro-8-methoxy-4-oxo-1,4-dihydro-3-quinolinecarboxylic acid (6.3 mmol) was used instead. JA 1007 was obtained in 88% yield as a brownish powder. Compound data:
Molecular Weight: 519.928; Composition: C(55.44%), H(4.65%), Cl(6.82%), F(7.31%), N(13.47%), O(12.31%);

NMR: 9.32, 8.61, 8.08, 7.83, 4.15, 4.02, 3.61, 3.43, 2.77, 1.90, 1.84, 1.22, 1.18, 1.00.

JA 1008 ($C_{25}H_{25}ClF_2N_4O_4$):

Prepared exactly as JA 1001, although 7-[3-(aminomethyl)-3-(fluoromethyl)-1-pyrrolidinyl]-1-cyclopropyl-6-fluoro-8-methoxy-4-oxo-1,4-dihydro-3-quinolinecarboxylic acid (6.3 mmol) was used instead of ciprofloxacin. JA 1008 was obtained in 86% yield as a brownish powder. Compound data:

Molecular Weight: 518.940; Composition: C(57.86%), H(4.86%), Cl(6.83%), F(7.32%), N(10.80%), O(12.33%); NMR: 9.67, 8.61, 7.83, 7.41, 7.07, 6.31, 4.15, 4.02, 3.61, 3.43, 2.79, 1.90, 1.84, 1.22, 1.18, 1.00.

JA 1009 ($C_{27}H_{27}F_3N_4O_4S$):

Prepared exactly as JA 1004, although 7-[3-(aminomethyl)-3-(fluoromethyl)-1-pyrrolidinyl]-1-cyclopropyl-6-fluoro-8-methoxy-4-oxo-1,4-dihydro-3-quinolinecarboxylic acid (6.3 mmol) was used instead. JA 1009 was obtained in 89% yield as a brownish powder. Compound data;

Molecular Weight: 560.589; Composition: C(57.85%), H(4.85%), F(10.17%), N(9.99%), O(11.42%), S(5.72%); NMR: 10.61, 8.61, 7.83, 7.19, 4.36, 4.22, 4.18, 4.02, 3.61, 3.42, 3.34, 3.23, 2.79, 1.91, 1.85, 1.22, 1.18, 1.00, 0.92.

JA 1010 ($C_{39}H_{33}F_3N_6O_{12}S_3$):

Prepared essentially as JA 2, although 1-cyclopropyl-6-fluoro-7-[3-({[(4-fluoroanilino)carbothioyl]amino}-methyl)-3-(fluoromethyl)-1-pyrrolidinyl]-8-methoxy-4-oxo-1,4-dihydro-3-quinolinecarboxylic acid (6.3 mmol) and an excess of 4-nitrobenzenesulfonyl chloride were used instead. JA 1010 was obtained in 82% yield as a creamy powder. Compound data:

Molecular Weight: 930.906; Composition: C(50.32%), H(3.57%), F(6.12%), N(9.03%), O(20.62%), S(10.33%); NMR: 14.41, 8.61, 8.46, 8.39, 7.83, 7.64, 7.51, 4.43, 4.30, 4.12, 4.02, 3.61, 3.44, 3.26, 2.79, 1.88, 1.18, 1.00.

JA 1012 ($C_{22}H21ClFN_7O_4$):

Prepared essentially as JA 39, although 7-[3-(aminomethyl)-4-(methoxyimino)-1-pyrrolidinyl]-1-cyclopropyl-6-fluoro-4-oxo-1,4-dihydro[1,8]naphthyridine-3-carboxylic acid (5.6 mmol) was used instead of ciprofloxacin. JA 1012 was obtained in 78% yield as a brownish powder. Compound data:

Molecular Weight: 501.898; Composition: C(52.65%), H(4.22%), Cl(7.06%), F(3.79%), N(19.54%) , O(12.75%). NMR: 9.77, 8.58, 8.31, 8.08, 7.79, 3.78, 3.64, 3.55, 3.11, 3.17, 1.18, 1.00.

JA 1013 ($C_{39}H_{36}F_2N_8O_{10}S_3$):

Prepared essentially as JA 2, although 1-cyclopropyl-6-fluoro-7-[3-({[(4-fluoroanilino)carbothioyl]amino}-methyl)-4-(methoxyimino)-1-pyrrolidinyl]-4-oxo-1,4-dihydro[1,8]naphthyridine-3-carboxylic acid (5.7 mmol) and an excess of 4-methoxybenzenesulfonyl chloride were used instead. JA 1010 was obtained in 68% yield as a creamy powder. Compound data:

Molecular Weight: 882.932; Composition: C(53.05%), H(4.11%), F(4.30%), N(9.52%), O(18.12%), S(10.90%) NMR: 14.41, 8.58, 8.24, 8.12, 7.64, 7.51, 7.02, 4.74, 4.63, 3.84, 3.78, 3.64, 3.37, 3.15, 1.18, 1.00.

JAP 200 ($C_{22}H_{19}Cl_2FN_4O_3$):

Prepared essentially as JA 42, although 7-(3-amino-1-pyrrolidinyl)-8-chloro-1-cyclopropyl-6-fluoro-4-oxo-1,4-dihydro-3-quinolinecarboxylic acid (5.6 mmol) was used instead of ciprofloxacin. JAP 200 was obtained in 88% yield as a creamy powder. Compound data:

Molecular Weight: 477.315; Composition: C(55.36%), H(4.01%), Cl(14.86%), F(3.98%), N(11.74%), O(10.06%); NMR: 10.79, 8.71, 8.16, 7.48, 7.02, 6.30, 3.99, 3.81, 3.66, 3.22, 1.98, 1.56, 1.17, 1.00.

JAP 201 ($C_{28}H_{22}Cl_2FN_5O_7S$):

Prepared essentially as JA 2, although 8-chloro-7-{3-[(6-chloro-2-pyridinyl)amino]-1-pyrrolidinyl}-1-cyclopropyl-6-fluoro-4-oxo-1,4-dihydro-3-quinolinecarboxylic acid (6.3 mmol) and an excess of 4-nitrobenzenesulfonyl chloride were used instead. JAP 201 was obtained in 86% yield as a creamy powder. Compound data:

Molecular Weight: 662.474; Composition: C(50.76%), H(3.35%), F(2.87%), N(10.57%), O(16.91%), S(4.84%); NMR: 14.41, 8.71, 8.16, 7.96, 7.67, 7.33, 6.63, 3.99, 3.8, 3.68, 3.29, 1.97, 1.53, 1.17, 1.00.

JAP 202 ($C_{27}H_{21}Cl_2FN_6O_7S$):

Prepared essentially as JA 2, although 8-chloro-7-{3-[(6-chloro-2-pyridinyl)amino]-1-pyrrolidinyl}-1-cyclopropyl-6-fluoro-4-oxo-1,4-dihydro-3-quinolinecarboxylic acid (5.6 mmol) and an excess of 4-nitrobenzenesulfonyl chloride were used instead. JAP 202 was obtained in 86% yield as a creamy powder. Compound data:

Molecular Weight: 663.462; Composition: C(48.88%), H(3.19%), Cl(10.69), F(2.86%), N(12.67%), O(16.88%), S(4.83%); NMR: 14.41, 8.74, 8.20, 7.93, 7.16, 6.73, 3.40, 3.33, 3.19, 3.12.

JAP 203 ($C_{26}H_{20}F_2N_4O_7S$):

Prepared essentially as JA 2, although 6-fluoro-1-(4-fluorophenyl)-4-oxo-7-(1-piperazinyl)-1,4-dihydro-3-quinolinecarboxylic acid (5.6 mmol; see U.S. Pat. No. 4,730,000) and an excess of 4-nitrobenzenesulfonyl chloride were used instead. JAP 203 was obtained in 84% yield as a creamy powder. Compound data:

Molecular Weight: 570.523; Composition: C(54.74%), H(3.53%), F(6.66%), N(9.82%), O(19.63%), S(5.62%); NMR: 14.41, 8.74, 8.20, 7.93, 7.16, 6.73, 3.40, 3.33, 3.19, 3.12.

JAP 204 ($C_{25}H_{19}ClF_2N_4O_3$):

Prepared essentially as JA 42, although 6-fluoro-1-(4-fluorophenyl)-4-oxo-7-(1-piperazinyl)-1,4-dihydro-3-quinolinecarboxylic acid (5.5 mmol) was used instead of ciprofloxacin. JAP 204 was obtained in 90% yield as a creamy powder. Compound data:

Molecular Weight: 496.893; Composition: C(60.43%), H(3.85%), Cl(7.13%), F(7.65%), N(11.28%), O(9.66%); NMR: 14.41, 8.74, 7.95, 7.59, 7.46, 6.73, 6.40, 3.90, 3.32.

JAP 205 ($C_{24}H_{18}ClF_2N_5O_3$):

Prepared essentially as JA 39, although 6-fluoro-1-(4-fluorophenyl)-4-oxo-7-(1-piperazinyl)-1,4-dihydro-3-quinolinecarboxylic acid (5.6 mmol) was used instead. JAP 205 was obtained in 77% yield as a brownish powder. Compound data:

Molecular Weight: 497.881; Composition: C(57.90%), H(3.64%), Cl(7.12%), F(7.63%), N(14.07%), O(9.64%); NMR: 14.41, 8.74, 8.06, 7.95, 7.59, 7.16, 6.73, 3.90, 3.32.

JAP 206 ($C_{22}H_{19}F_3N_4O_7S$):

Prepared essentially as JA 2, although 6,8-difluoro-1-(2-fluoroethyl)-7-(4-methyl-1-piperazinyl)-4-oxo-1,4-dihydro-3-quinolinecarboxylic acid (5.6 mmol; see U.S. Pat. No. 4,398,029) and an excess of 4-nitrobenzenesulfonyl chloride were used instead. JAP 206 was obtained in 85% yield as a creamy powder. Compound data:

Molecular Weight: 540.470; Composition: C(48.89%), H(3.54%), F(10.55%), N(10.37%), O(20.72%), S(5.93%); NMR: 14.41, 9.66, 8.20, 7.93, 7.86, 4.77, 4.66, 3.62, 3.54, 3.40, 3.16, 3.09.

JAP 207 ($C_{21}H_{18}ClF_3N_4O_3$):

Prepared essentially as JA 42, although 6,8-difluoro-1-(2-fluoroethyl)-7-(4-methyl-1-piperazinyl)-4-oxo-1,4-dihydro- 3-quinolinecarboxylic acid (5.6 mmol) was used instead. JAP 207 was obtained in 90% yield as a creamy powder. Compound data:

Molecular Weight: 466.841; Composition: C(54.03%), H(3.89%), Cl(7.59%), F(12.21%), N(12.00%), O(10.28%); NMR: 14.41, 9.66, 7.90, 7.46, 7.01, 6.40, 4.77, 4.66, 3.90, 3.85, 3.62, 3.54, 3.44.

JAP 208 ($C_{20}H_{17}ClF_3N_5O_3$):

Prepared essentially as JA 39, although 6,8-difluoro-1-(2-fluoroethyl)-7-(4-methyl-1-piperazinyl)-4-oxo-1,4-dihydro-3-quinolinecarboxylic acid (5.6 mmol) was used instead. JAP 208 was obtained in 77% yield as a brownish powder. Compound data:

Molecular Weight: 467.829; Composition: C(51.35%), H(3.66%), Cl(7.58%), F(12.18%), N(14.97%), O(10.26%); NMR: 14.41, 9.66, 8.06, 7.90, 4.77, 4.66, 3.90, 3.62, 3.54, 3.44.

JAP 209 ($C_{25}H_{25}FN_4O_7S$):

Prepared essentially as JA 2, although 1-cyclopropyl-6-fluoro-5-methyl-7-(3-methyl-1-piperazinyl)-4-oxo-1,4-dihydro-3-quinolinecarboxylic acid (5.6 mmol; see U.S. Pat. No. 4,920,120) and an excess of 4-nitrobenzenesulfonyl chloride were used instead. JAP 209 was obtained in 87% yield as a creamy powder. Compound data:

Molecular Weight: 544.553; Composition: C(55.14%), H(4.63%), F(3.49%), N(10.29%), O(20.57%), S(5.89%); NMR: 14.41, 8.65, 8.20, 7.90, 7.46, 4.11, 3.46, 3.41, 3.17, 2.58, 2.09, 1.23, 1.17, 1.00.

JAP 210 ($C_{24}H_{24}ClFN_4O_3$):

Prepared essentially as JA 42, although 1-cyclopropyl-6-fluoro-5-methyl-7-(3-methyl-1-piperazinyl)-4-oxo-1,4-dihydro-3-quinolinecarboxylic acid (5.6 mmol) was used instead of ciprofloxacin. JAP 210 was obtained in 82% yield as a creamy powder. Compound data:

Molecular Weight: 470.924; Composition: C(61.21%), H(5.14%), Cl(7.53%), F(4.03%), N(11.90%), O(10.19%); NMR: 14.41, 8.65, 8.20, 7.90, 7.46, 4.11, 3.46, 3.41, 3.17, 2.58, 2.09, 1.23, 1.17, 1.00.

JAP 211 ($C_{23}H_{23}ClFN_5O_3$):

Prepared essentially as JA 39, although 1-cyclopropyl-6-fluoro-5-methyl-7-(3-methyl-1-piperazinyl)-4-oxo-1,4-dihydro-3-quinolinecarboxylic acid (5.6 mmol) was used instead. JAP 211 was obtained in 79% yield as a brownish powder. Compound data:

Molecular Weight: 467.829; Composition: C(58.54%), H(4.91%), Cl(7.51%), F(4.03%), N(14.84%), O(10.17%); NMR: 14.41, 8.65, 8.04, 7.13, 4.21, 4.00, 4.11, 3.83, 3.24, 2.82, 2.09, 1.33, 1.17, 1.00.

JAP 213 ($C_{23}H_{22}F_2N_4O_7S$):

Prepared essentially as JA 2, although 1-ethyl-6,8-difluoro-7-(3-methyl-1-piperazinyl)-4-oxo-1,4-dihydro-3-quinolinecarboxylic acid (5.6 mmol; see U.S. Pat. No. 4,528,287) and an excess of 4-nitrobenzenesulfonyl chloride were used instead. JAP 213 was obtained in 89% yield as a creamy powder. Compound data:

Molecular Weight: 536.506; Composition: C(51.49%), H(4.13%), F(7.08%), N(10.44%), O(20.88%), S(5.98%); NMR: 14.41, 9.02, 8.20, 7.90, 7.83, 4.51, 3.46, 3.41, 3.14, 2.55, 1.55, 1.23.

JAP 214 ($C_{22}H_{21}ClF_2N_4O_3$):

Prepared essentially as JA 42, although 1-ethyl-6,8-difluoro-7-(3-methyl-1-piperazinyl)-4-oxo-1,4-dihydro-3-quinolinecarboxylic acid (5.6 mmol) was used instead. JAP 210 was obtained in 85% yield as a creamy powder. Compound data:

Molecular Weight: 462.877; Composition: C(57.09%), H(4.57%), Cl(7.66%), F(8.21%), N(12.10%), O(10.37%); NMR: 14.41, 9.02, 7.85, 7.43, 7.02, 6.38, 4.51, 4.20, 3.97, 3.40, 3.33, 3.22, 2.79, 1.55, 1.33.

JAP 215 ($C_{23}H_{21}FN_4O_8S$):

Prepared essentially as JA 2, although 9-fluoro-3-methyl-7-oxo-10-(1-piperazinyl)-2,3-dihydro-7H-[1,4]oxazino[2,3,4-ij]quinoline-6-carboxylic acid (5.6 mmol; see U.S. Pat. No. 4,382,892) and an excess of 4-nitrobenzenesulfonyl chloride were used instead. JAP 215 was obtained in 89% yield as a creamy powder. Compound data:

Molecular Weight: 532.499; Composition: C(51.88%), H(3.97%), F(3.57%), N(10.52%), O(24.04%), S(6.02%); NMR: 14.41, 8.57, 7.99, 4.42, 3.82, 3.53, 3.40, 3.33, 1.35.

JAP 216 ($C_{22}H_{20}ClFN_4O_4$):

Prepared essentially as JA 42, although 9-fluoro-3-methyl-7-oxo-10-(1-piperazinyl)-2,3-dihydro-7H-[1,4]oxazino[2,3,4-ij]quinoline-6-carboxylic acid (5.6 mmol) was used instead. JAP 216 was obtained in 86% yield as a creamy powder. Compound data:

Molecular Weight: 458.870; Composition: C(57.58%), H(4.39%), Cl(7.73%), F(4.14%), N(12.21%), O(13.95%); NMR: 14.41, 8.57, 7.99, 7.46, 7.01, 6.40, 4.42, 3.84, 3.53, 2.86, 1.35.

JAP 217 ($C_{21}H_{19}ClFN_5O_4$):

Prepared essentially as JA 39, although 9-fluoro-3-methyl-7-oxo-10-(1-piperazinyl)-2,3-dihydro-7H-[1,4]oxazino[2,3,4-ij]quinoline-6-carboxylic acid (5.6 mmol) was used instead. JAP 217 was obtained in 80% yield as a brownish powder. Compound data:

Molecular Weight: 459.858; Composition: C(54.85%), H(4.16%), Cl(7.71%), F(4.13%), N(15.23%), O(13.92%); NMR: 14.41, 8.57, 8.06, 7.95, 4.42, 3.82, 3.53, 2.86, 1.35.

JAP 218 ($C_{22}H_{19}FN_4O_7S_2$):

Prepared essentially as JA 2, although 9-fluoro-7-oxo-10-(1-piperazinyl)-2,3-dihydro-7H-[1,4]thiazino[2,3,4-ij]quinoline-6-carboxylic acid (5.6 mmol; see U.S. Pat. No. 4,684,647) and an excess of 4-nitrobenzenesulfonyl chloride were used instead. JAP 218 was obtained in 89% yield as a creamy powder. Compound data:

Molecular Weight: 534.539; Composition: C(49.43%), H(3.58%), F(3.55%), N(10.48%), O(20.95%), S(12.00%); NMR: 14.41, 8.93, 8.20, 7.93, 7.35, 4.49, .4.42, 3.40, 3.24, 2.95, 3.12.

JAP 219 ($C21H_{18}ClFN_4O_3S$):

Prepared essentially as JA 42, although 9-fluoro-7-oxo-10-(1-piperazinyl)-2,3-dihydro-7H-[1,4]thiazino[2,3,4-ij]quinoline-6-carboxylic acid (5.6 mmol) was used instead. JAP 219 was obtained in 84% yield as a creamy powder. Compound data:

Molecular Weight: 460.910; Composition: C(54.72%), H(3.94%), Cl(7.6996), F(4.12%), N(12.12%), O(10.41%), S(6.96); NMR: 14.41, 8.93, 7.46, 7.35, 7.01, 6.40, 4.49, 4.42 3.90, 3.24, 2.95.

JAP 220 ($C_{20}H_{17}ClFN_5O_3S$):

Prepared essentially as JA 39, although 9-fluoro-7-oxo-10-(1-piperazinyl)-2,3-dihydro-7H-[1,4]thiazino[2,3,4-ij]quinoline-6-carboxylic acid (5.6 mmol) was used instead. JAP 220 was obtained in 76% yield as a brownish powder. Compound data:

Molecular Weight: 461.898; Composition: C(52.01%), H(3.71%), Cl(7.68%), F(4.11%), N(15.16), O(10.39%), S(6.94); NMR: 14.41, 8.93, 8.06, 7.35, 4.49, 4.42, 3.90, 3.24, 2.95.

JAP 221 ($C_{29}H_{24}F_2N_6O_{11}S_2$):

Prepared essentially as JA 2, although 5-amino-1-cyclopropyl-6,8-difluoro-4-oxo-7-(1-piperazinyl)-1,4-dihydro-3-quinolinecarboxylic acid (5.6 mmol; see U.S. Pat. No. 4,795,751) and an excess of 4-nitrobenzenesulfonyl chloride were used instead. JAP 221 was obtained in 83% yield as a creamy powder. Compound data:

Molecular Weight: 734.664; Composition: C(47.41%), H(3.29%), F(5.17%), N(11.44%), O(23.96%), S(8.73%); NMR: 14.92, 8.84, 8.20, 7.93, 4.26, 3.40, 3.33, 3.16, 3.09, 1.17, 1.00.

JAP 222 ($C_{31}H_{28}F_2N_6O_{11}S_2$):

Prepared essentially as JA 2, although 5-amino-1-cyclopropyl-7-(3,5-dimethyl-1-piperazinyl)-6,8-difluoro-4-oxo-1,4-dihydro-3-quinolinecarboxylic acid (5.6 mmol; see U.S. Pat. No. 4,795,751) and an excess of 4-nitrobenzenesulfonyl chloride were used instead. JAP 222 was obtained in 81% yield as a creamy powder. Compound data:

Molecular Weight: 762.717; Composition: C(48.82%), H(3.70%), F(4.98%), N(11.02%), O(23.07%), S(8.41%); NMR: 14.92, 8.84, 8.21, 7.87, 4.26, 3.58, 3.00, 2.52, 1.23, 1.17, 1.00.

JAP 223 ($C_{29}H_{26}Cl_2F_2N_6O_3$):

Prepared essentially as JA 42, although 5-amino-1-cyclopropyl-7-(3,5-dimethyl-1-piperazinyl)-6,8-difluoro-4-oxo-1,4-dihydro-3-quinolinecarboxylic acid (5.6 mmol) was used instead. JAP 223 was obtained in 80% yield as a creamy powder. Compound data:

Molecular Weight: 615.458; Composition: C(56.59%), H(4.26%), Cl(11.52%), F(6.17%), N(13.65%), O(7.80%); NMR: 14.52, 8.84, 7.79, 7.40, 7.09, 6.36, 4.26, 3.88, 3.20, 2.77, 1.34, 1.17, 1.00.

JAP 224 ($C_{27}H_{24}Cl_2F_2N_8O_3$):

Prepared essentially as JA 39, although 5-amino-1-cyclopropyl-7-(3,5-dimethyl-1-piperazinyl)-6,8-difluoro-4-oxo-1,4-dihydro-3-quinolinecarboxylic acid (5.6 mmol) was used instead. JAP 220 was obtained in 76% yield as a brownish powder. Compound data:

Molecular Weight: 617.434; Composition: C(52.52%), H(3.92%), Cl(11.48%), F(6.15%), N(18.15), O(7.77%); NMR: 15.62, 8.84, 8.36, 8.03, 4.26, 3.88, 3.20, 2.77, 1.34, 1.17, 1.00.

JAP 225 ($C27H_{21}F_3N_4O_7S$):

Prepared essentially as JA 2, although 1-(2,4-difluorophenyl)-6-fluoro-7-(3-methyl-1-piperazinyl)-4-oxo-1,4-dihydro-3-quinolinecarboxylic acid (5.6 mmol; see U.S. Pat. No. 4,730,000) and an excess of 4-nitrobenzenesulfonyl chloride were used instead. JAP 225 was obtained in 81% yield as a creamy powder. Compound data:

Molecular Weight: 602.540; Composition: C(53.82%), H(3.51%), F(9.46%), N(9.30%), O(18.59%), S(5.32%); NMR: 14.41, 8.93, 8.20, 8.06, 7.90, 7.08, 6.79, 6.59, 3.48, 3.41, 3.17, 2.58, 1.23.

JAP 226 ($C_{25}H_{19}ClF_3N_5O_3$):

Prepared essentially as JA 39, although 1-(2,4-difluorophenyl)-6-fluoro-7-(3-methyl-1-piperazinyl)-4-oxo-1,4-dihydro-3-quinolinecarboxylic acid (5.6 mmol) was used instead. JAP 226 was obtained in 78% yield as a brownish powder. Compound data:

Molecular Weight: 529.898; Composition: C(56.67%), H(3.61%), Cl(6.69%), F(10.76%), N(13.22), O(9.06%); NMR: 14.41, 8.93, 8.04, 7.59, 7.08, 6.79, 6.59, 4.24, 4.00, 3.29, 2.82, 1.33.

JAP 227 ($C26H_{20}ClF_3N_4O_3$):

Prepared essentially as JA 42, although 1-(2,4-difluorophenyl)-6-fluoro-7-(3-methyl-1-piperazinyl)-4-oxo-1,4-dihydro-3-quinolinecarboxylic acid (5.6 mmol) was used instead. JAP 227 was obtained in 83% yield as a creamy powder. Compound data:

Molecular Weight: 528.910; Composition: C(59.04%), H(3.81%), Cl(6.70%), F(10.78%), N(10.59%), O(9.07%); NMR: 14.41, 8.93, 8.05, 7.59, 7.43, 7.02, 6.38, 4.24, 4.00, 3.29, 2.82, 1.33.

As for the preparation of the other compounds according to the present invention, useful general guidance is also provided by the following publications: EP 195 316 A1; U.S. Pat. Nos. 4,398,029; 4,528,287; 4,684,647; 4,730,000; 4,795,751; 4,920,120; 5,164,402; 5,677,316; 5,776,944; Org. Syntheses, Coll. Vol. 2, 586, pp. 1055–1057 (1943); ibid., 34–38, 179–183, 943–946; "Advanced Organic Chemistry", March, J., p.445 and pp. 802–803, $3^{rd}$ ed.

The synthesis of the required starting substances is readily accomplished by a person skilled in the art, should they not be commercially available. The additional compounds listed below were all prepared by using essentially the same synthetic protocol as that used for the previously disclosed compounds.

B700 ($C_{24}H_{22}FN_5O_6$):

1-cyclopropyl-6-fluoro-7-{4-[(4-nitroanilino) carbonyl]-1-piperazinyl}-4-oxo-1,4-dihydro-3-quinolinecarboxylic acid;

B702 ($C_{24}H_{23}F_2N_5O_6$):

1-ethyl-6,8-difluoro-7-{3-methyl-4-[(4-nitroanilino) carbonyl]-1-piperazinyl}-4-oxo-1,4-dihydro-3-quinolinecarboxylic acid;

JA 41 ($C_{23}H_{21}ClFN_3O_3S$):

7-[4-(3-chloro-2-sulfanylphenyl)-1-piperazinyl]-1-cyclopropyl-6-fluoro-4-oxo-1,4-dihydro-3-quinolinecarboxylic acid;

JA 47-2 ($C_{30}H_{21}F_3N_4O_7S_2$):

1-cyclopropyl-6-fluoro-7-[[(4-fluorophenyl)sulfonyl] (6-{[(4-fluorophenyl)sulfonyl]amino}-2-pyridinyl) amino]-4-oxo-1,4-dihydro-3-quinolinecarboxylic acid;

JA 53-2 ($C_{30}H_{25}F_3N_4)_5S_2$):

1-cyclopropyl-6-fluoro-7-[4-({4-fluoro[(4-fluorophenyl)sulfonyl]anilino}carbothioyl)-1-piperazinyl]-4-oxo-1,4-dihydro-3-quinolinecarboxylic acid;

JA 53-3 ($C_{30}H_{25}F_2N_5O_7S_2$):

1-cyclopropyl-6-fluoro-7-[4-({4-fluoro[(4-nitrophenyl)sulfonyl]anilino}carbothioyl)-1-piperazinyl]-4-oxo-1,4-dihydro-3-quinolinecarboxylic acid;

JA 53-5 ($C_{28}H_{23}ClF_2N_6O_3S$):

7-(4-{[(6-chloro-2-pyrazinyl)-4-fluoroanilino] carbothioyl}-1-piperazinyl)-1-cyclopropyl-6-fluoro-4-oxo-1,4-dihydro-3-quinolinecarboxylic acid;

JA 53-6 ($C_{29}H_{24}ClF_2N_5O_3S$):

7-(4-{[(6-chloro-2-pyridinyl)-4-fluoroanilino] carbothioyl}-1-piperazinyl)-1-cyclopropyl-6-fluoro-4-oxo-1,4-dihydro-3-quinolinecarboxylic acid;

JA 69-2 ($C_{24}H_{22}ClFN_4O_5$):

7-[(4-carboxycyclohexyl)(6-chloro-2-pyrazinyl) amino]-1-cyclopropyl-6-fluoro-4-oxo-1,4-dihydro-3-quinolinecarboxylic acid;

JA 69-3 ($C_{21}H_{20}F_4N_2O_7S$):

7-{(4-carboxycyclohexyl) [(trifluoromethyl) sulfonyl]-amino}-1-cyclopropyl-6-fluoro-4-oxo-1,4-dihydro-3-quinolinecarboxylic acid;

JA 74-2 ($C_{21}H_{21}FN_2O_3$):

1-ethyl-6-fluoro-7-(4-isopropylanilino)-4-oxo-1,4-dihydro-3-quinolinecarboxylic acid;

JA 76-2 ($C_{26}H_{27}FN_4O_7S$):

1-cyclopropyl-6-fluoro-7-{[(4-nitrophenyl)sulfonyl][2-(1-piperidinyl)ethyl]amino}-4-oxo-1,4-dihydro-3-quinolinecarboxylic acid;

JA 76-3 ($C_{24}H_{25}ClFN_5O_3$):

7-{(6-chloro-2-pyrazinyl)[2-(1-piperidinyl)ethyl]amino}-1-cyclopropyl-6-fluoro-4-oxo-1,4-dihydro-3-quinolinecarboxylic acid;

JA 79-2 ($C_{29}H_{26}F_3N_3O_7S_4$):

1-cyclopropyl-6-fluoro-7-([(4-fluorophenyl)sulfonyl]{2-[(2-{[(4-fluorophenyl)sulfonyl]amino}ethyl)disulfanyl]-ethyl}amino)-4-oxo-1,4-dihydro-3-quinolinecarboxylic acid;

JA 79-3 ($C_{29}H_{26}FN_5O_{11}S_4$):

1-cyclopropyl-6-fluoro-7-([(4-nitrophenyl)sulfonyl]{2-[(2{[(4-nitrophenyl)sulfonyl]amino}ethyl)disulfaryl]-ethyl}amino)-4-oxo-1,4-dihydro-3-quinolinecarboxylic acid;

JA 82-2 ($C_{30}H_{28}FN_5O_{13}S_2$):

1-cyclopropyl-6-fluoro-7-{[(4-nitrophenyl)sulfonyl]{2-[2-({[(4-nitrophenyl)sulfonyl]amino}methoxy)ethoxy]ethyl}-amino)-4-oxo-1,4-dihydro-3-quinolinecarboxylic acid;

JA 82-3 ($C_{26}H_{24}Cl_2FN_7O_5$):

7-{(6-chloro-2-pyrazinyl)[2-(2-{[(6-chloro-2-pyrazinyl)amino]methoxy}ethoxy)ethyl]amino}-1-cyclopropyl-6-fluoro-4-oxo-1,4-dihydro-3-quinolinecarboxylic acid;

JA 96-2 ($C_{38}H_{32}F_2N6O_{12}S_2$):

1-cyclopropyl-6-fluoro-7-[4-({({4-fluoro[(4-nitrophenyl)sulfonyl]anilino}carbonyl)[(4-nitrophenyl)sulfonyl]amino}methyl)-1-piperidinyl]-4-oxo-1,4-dihydro-3-quinolinecarboxylic acid;

JA 97 ($C_{19}H_{22}FN_3O_3$):

1-cyclopropyl-6-fluoro-4-oxo-7-{[2-(1-pyrrolidinyl)ethyl]amino}-1,4-dihydro-3-quinolinecarboxylic acid;

JA 97-2 ($C_{26}H_{26}FN_5O_5S$):

1-cyclopropyl-6-fluoro-7-{[(4-nitroanilino)carbothioyl][2-(1-pyrrolidinyl)ethyl]amino}-4-oxo-1,4-dihydro-3-quinolinecarboxylic acid;

JA 97-3 ($C_{23}H_{23}ClFN_5O_3$):

7-{(6-chloro-2-pyrazinyl)[2-(1-pyrrolidinyl)ethyl]amino}-1-cyclopropyl-6-fluoro-4-oxo-1,4-dihydro-3-quinolinecarboxylic acid;

JA 97-4 ($C_{25}H_{25}FN_4O_7S$):

1-cyclopropyl-6-fluoro-7-{([4-nitrophenyl)sulfonyl][2-(1-pyrrolidinyl)ethyl]amino}-4-oxo-1,4-dihydro-3-quinolinecarboxylic acid;

JA 97-5 ($C_{20}H_{21}F_4N_3O_5S$):

1-cyclopropyl-6-fluoro-4-oxo-7-{[2-(1-pyrrolidinyl)ethyl][(trifluoromethyl)sulfonyl]amino}-1,4-dihydro-3-quinolinecarboxylic acid;

JA 99-2 ($C_{33}H_{32}F_3N_3O_7S_2$):

1-cyclopropyl-6-fluoro-7-([(4-fluorophenyl)sulfonyl]{[3-({[(4-fluorophenyl)sulfonyl]amino}methyl)cyclohexyl]methyl}amino)-4-oxo-1,4-dihydro-3-quinolinecarboxylic acid;

JA 102 ($C_{20}H_{27}FN_4O_3$):

7-({3-[(3-aminopropyl)(methyl)amino]propyl}amino)-1-cyclopropyl-6-fluoro-4-oxo-1,4-dihydro-3-quinolinecarboxylic acid;

JA 103-2 ($C_{18}H_{16}F_7N_3O_7S_2$):

1-cyclopropyl-6-fluoro-4-oxo-7-[[(trifluoromethyl)sulfonyl](3-{[(trifluoromethyl)sulfonyl]amino}propyl)amino]-1,4-dihydro-3-quinolinecarboxylic acid;

JA 103-3 ($C_{28}H_{24}FN_5O_{11}S_2$):

1-cyclopropyl-6-fluoro-7-[[(4-nitrophenyl)sulfonyl](3-{[(4-nitrophenyl)sulfonyl]amino}propyl)amino]-4-oxo-1,4-dihydro-3-quinolinecarboxylic acid;

JA 104-2 ($C_{21}H_{25}F_4N_3O_5S$):

1-cyclopropyl-7-{[3-(dimethylamino)-2,2-dimethylpropyl][(trifluoromethyl)sulfonyl]amino}-6-fluoro-4-oxo-1,4-dihydro-3-quinolinecarboxylic acid;

JA 104-3 ($C_{25}H_{28}FN_3O_4S$):

1-cyclopropyl-7-[(3-(dimethylamino)-2,2-dimethylptopyl]-(2-thienylcarbonyl)aminol-6-fluoro-4-oxo-1,4-dihydro-3-quinolinecarboxylic acid;

JA 106-3 ($C_{17}H_{14}F_7N_3O_7S_2$):

1-cyclopropyl-6-fluoro-4-oxo-7-[[(trifluoromethyl)sulfonyl](2-{[(trifluoromethyl)sulfonyl]amino}ethyl)amino]-1,4-dihydro-3-quinolinecarboxylic acid;

JA 106-4 ($C_{27}H_{22}FN_5O_{11}S_2$):

1-cyclopropyl-6-fluoro-7-[[(4-nitrophenyl)sulfonyl](2-{[(4-nitrophenyl)sulfonyl]amino}ethyl)amino]-4-oxo-1,4-dihydro-3-quinolinecarboxylic acid;

JA 107-2 ($C_{20}H_{20}F_7N_3O_7S_2$):

1-cyclopropyl-7-{(2,2-dimethyl-3-{[(trifluoromethyl)sulfonyl]amino}propyl)[(trifluoromethyl)sulfonyl]amino}-6-fluoro-4-oxo-1,4-dihydro-3-quinolinecarboxylic acid;

JA 110 ($C_{28}H_{27}FN_4O_3S$):

7-(4-{[(anilinocarbothioyl)amino]methyl}-1-piperidinyl)-1-cyclopropyl-6-fluoro-4-oxo-1,4-dihydro-3-quinolinecarboxylic acid;

JA 124 ($C_{23}H_{17}FN_2O_5S$):

1-cyclopropyl-6-fluoro-7[(2-furylmethyl)(2-thienylcarbonyl)amino]-4-oxo-1,4-dihydro-3-quinolinecarboxylic acid;

JA 128 ($C_{25}H_{26}FN_3O_4S$):

1-cyclopropyl-6-fluoro-4-oxo-7-[[2-(1-piperidinyl)ethyl]-(2-thienylcarbonyl)amino]-1,4-dihydro-3-quinolinecarboxylic acid;

JA 140 ($C_{23}H_{21}FN_2O_5S$):

1-cyclopropyl-6-fluoro-4-oxo-7-[(tetrahydro-2-furanylmethyl)(2-thienylcarbonyl)amino]-1,4-dihydro-3-quinolinecarboxylic acid;

JA 148 ($C_{21}H_{23}FN_2O_6$):

7-[acetoacetyl(2-methoxy-1-methylethyl)amino]-1-cyclopropyl-6-fluoro-4-oxo-1,4-dihydro-3-quinolinecarboxylic acid;

JA 149 ($C_{23}H_{22}FN_3O_8S$):

1-cyclopropyl-6-fluoro-7-{(2-methoxy-1-methylethyl)[(4-nitrophenyl)sulfonyl]amino}-4-oxo-1,4-dihydro-3-quinolinecarboxylic acid.

μg/ml. The volume (ml) used of 10% KOH and DMF for dissolution of each respective test compound is given in Table 1 below.

In this evaluation, the antibacterial activity of the present compounds and enrofloxacin as reference compound was tested against seven strains of gram-positive bacteria, namely *Bacillus subtilus* (ATCC 6633), *Bacillus cereus, Streptococcus faecium, Micrococcus Luteus* (ATCC 9341), *Staph. aureus* (ATCC 29737), *Staph. epidermidis* (ATCC 12228) and *Staphylococcus* (ATCC 6538). The results are presented in the following Table 6.

TABLE 6

M.I.C. values for compounds tested

| Compound tested | KOH/DMF (ml) | Bacillus subtilus | Bacillus cereus | Streptoc. faecium | Microc. Luteus | Staph. aureus | Staph. epidermidis | Staph. (ATCC 6538) |
|---|---|---|---|---|---|---|---|---|
| Enrofloxacin | 0.10/0.10 | 0.500 | 0.250 | 1.000 | 2.000 | 0.250 | 0.120 | 0.120 |
| JA 1 | 0.14/1.50 | 0.060 | 0.060 | 0.500 | 0.500 | 0.120 | 0.060 | 0.060 |
| JA 2 | 0.10/0.70 | 0.120 | 0.060 | 0.500 | 0.500 | 0.120 | 0.060 | 0.030 |
| JA 3 | 0.10/— | 0.060 | 0.060 | 0.250 | 1.000 | 0.060 | 0.010 | 0.060 |
| JA 4 | 0.10/0.10 | 0.010 | 0.010 | 0.060 | 0.250 | 0.060 | 0.030 | 0.010 |
| JA 5 | 0.10/0.50 | 0.008 | 0.030 | 0.120 | 0.500 | 0.060 | 0.010 | 0.060 |
| JA 9 | 0.14/0.50 | 0.250 | 0.250 | 1.000 | 1.000 | ≧0.120 | 0.120 | 0.060 |
| JA 10 | 0.10/— | 0.500 | 0.120 | 1.000 | 2.000 | 0.250 | 0.250 | 0.250 |
| JA 12 | 0.10/0.50 | 0.120 | 0.060 | 1.000 | 0.500 | 0.120 | 0.120 | 0.030 |
| JA 21 | 0.10/— | 0.250 | 0.010 | 0.500 | 2.000 | 0.250 | 0.060 | 0.060 |
| JA 39 | 0.10/0.50 | 0.060 | 0.010 | 0.250 | 1.000 | 0.120 | 0.010 | 0.030 |
| JA 40 | 0.12/1.00 | 0.120 | 0.060 | 1.000 | 2.000 | 0.250 | 0.120 | 0.060 |
| JA 41 | 0.16/1.70 | 0.500 | 0.250 | 1.000 | 2.000 | 0.250 | 0.250 | 0.250 |
| JA 42 | 0.10/1.70 | 0.010 | 0.060 | 0.250 | 1.000 | 0.030 | 0.008 | 0.060 |
| JA 43 | 0.10/1.00 | 0.250 | 0.120 | 1.000 | 1.000 | 0.120 | 0.250 | 0.030 |
| JA 46 | 0.14/1.00 | 0.120 | 0.060 | 0.500 | 1.000 | 0.120 | 0.120 | 0.120 |
| JA 68 | 0.10/1.00 | 0.120 | 0.060 | 1.000 | 2.000 | 0.120 | 0.250 | 0.120 |
| JA 69 | 0.16/1.00 | 0.120 | 0.060 | 2.000 | 2.000 | 0.120 | 0.120 | 0.120 |
| JA 70 | 0.10/0.50 | 0.250 | 0.120 | 2.000 | 1.000 | 0.120 | 0.250 | 0.120 |
| JA 73 | 0.16/1.00 | 0.120 | 0.060 | 0.500 | 2.000 | 0.120 | 0.120 | 0.060 |
| JA 74 | 0.14/1.00 | 0.120 | 0.120 | 2.000 | 2.000 | 0.120 | 0.120 | 0.120 |
| JA 76 | 0.10/1.00 | 0.120 | 0.120 | 1.000 | 2.000 | 0.120 | 0.120 | 0.060 |
| JA 102 | 0.14/1.00 | 0.120 | 0.060 | 1.000 | 2.000 | 0.060 | 0.120 | 0.120 |
| JA 124 | 0.10/1.00 | 0.120 | 0.120 | 1.000 | 2.000 | 0.120 | 0.120 | 0.120 |
| JA 128 | 0.10/1.20 | 0.120 | 0.060 | 1.000 | 2.000 | 0.120 | 0.060 | 0.120 |
| JA 135 | 0.14/1.50 | 0.120 | 0.060 | 0.500 | 2.000 | 0.120 | 0.120 | 0.120 |
| JA 136 | 0.10/1.50 | 0.120 | 0.060 | 0.500 | 2.000 | 0.120 | 0.120 | 0.120 |
| JA 137 | 0.10/0.10 | 0.120 | 0.250 | 1.000 | 2.000 | 0.500 | 0.250 | 0.120 |
| JA 138 | 0.10/1.00 | 0.120 | 0.060 | 1.000 | 2.000 | 0.250 | 0.120 | 0.120 |
| JA 140 | 0.10/1.00 | 0.060 | 0.060 | 0.500 | 1.000 | 0.120 | 0.120 | 0.060 |
| JA 141 | 0.10/— | 0.120 | 0.120 | 1.000 | 2.000 | 0.250 | 0.120 | 0.120 |
| JA 143 | 0.10/0.10 | 0.120 | 0.120 | 1.000 | >2.000 | 0.250 | 0.120 | 0.120 |
| JA 144 | 0.10/1.00 | 0.120 | 0.120 | 0.500 | 1.000 | 0.120 | 0.120 | 0.060 |
| JA 145 | 0.16/1.30 | 0.120 | 0.120 | 1.000 | 2.000 | 0.120 | 0.120 | 0.120 |
| JA 146 | 0.10/1.00 | 0.120 | 0.120 | 1.000 | 2.000 | 0.120 | 0.120 | 0.120 |
| JA 148 | 0.10/0.50 | 0.120 | 0.060 | 1.000 | 2.000 | 0.120 | 0.120 | 0.120 |
| JA 149 | 0.10/0.50 | 0.120 | 0.120 | 2.000 | 2.000 | 0.120 | 0.120 | 0.120 |

Biological Evaluation of the Present Compounds

Antibacterial Testing Against Gram-positive and Gram-negative Bacteria:

The antibacterial activity of the present compounds was investigated by in vitro evaluation of their M.I.C. (Minimum Inhibitory Concentration) values. The evaluation was conducted in complete accordance with the "Broth dilution method", as outlined by the U.S. National Committee for Clinical Laboratory Standards "NCCLS 1988".

Solutions of the present compounds were prepared by dissolving 0.01 g of a test compound in either 10% KOH (aq) or a 10% KOH/DMF mixture, after which sterile, distilled $H_2O$ was added up to a total volume of 10 ml, thereby yielding a test compound concentration of 1 000

As is evident from Table 6 above, the compounds according to the present invention have excellent antibacterial properties. Indeed, the antibacterial activity of the present compounds against gram-positive S bacteria is at least equal, and in some instances even clearly superior (e.g. JA 4 and JA 39), to that of enrofloxacin.

In the same manner as above, the M.I.C. values of the present compounds JA 3, JA 5, JA 12, JA 42, JA 73 and enrofloxacin as reference compound were investigated also on gram-negative bacteria. The gram-negative bacteria used were *E. coli* (ATCC 25922), *E. Coli* (ATCC 8739), *E. Coli* (ATCC 10536), *E. Coli* Pathogenic, *KL. Pnemonia* (ATCC 10031), *Bordetella bronchiseptic* (ATCC 4617), *Salmonella* typhi, Salmonella spp., *Proteus* spp., *Pasterulla* Duck and *Pasterulla* Camel. In summary, it was found that all of said present compounds have antibacterial activity against gram-negative bacteria, and that their activity is roughly equal to that of enrofloxacin.

Antibacterial Testing Against *Mycoplasma*:

As is well known, *Mycoplasma* are bacteria which often cause severe respiratory tract infections in both humans and animals. As typical examples, an infection of *M. pneumoniae* in humans causes pneumonia, whereas an infection of *M. gallisepticum* in avians, especially chickens, normally causes chronic respiratory disease or sinusitis.

The M.I.C. values of the compounds JA 1, JA 3, JA 5, JA 12, JA 42 and JA 43 were determined in vitro against *M. gallisepticum*. Enrofloxacin, tylosin and oxytetracyclin were used as reference compounds. The tested compounds were all stored and applied as solutions in distilled water. The M.I.C. evaluation was performed in microtitre plates, and the methodology employed was basically that of Tanner and Wu (Avian Disease, 36:714–717 (1992)). The results are presented in Table 7 below:

TABLE 7

M.I.C. values against *M. gallisepticum*

| Compound tested | M.I.C. values |
| --- | --- |
| JA 1 | 0.03 |
| JA 3 | 0.06 |
| JA 5 | 0.12 |
| JA 12 | 0.12 |
| JA 42 | 0.25 |
| JA 43 | 0.25 |
| Enrofloxacin | 0.06 |
| Tylosin | 0.06 |
| Oxytetracyclin | 0.12 |

As can be seen in Table 7, the present compounds have antibacterial activity against *M. gallisepticum* as well, and the high antibacterial activity of JA 1 is noteworthy.

Antiparasitic Testing Against *Coccidia*:

The anticoccidial activity of the present compounds as prophylactic agents was evaluated in vivo on 60 one day old (1 day after hatch) chickens of Habbared X breed. The chickens were divided into four groups of 20 birds each, and each group was located in a separate pen (1 m×1 m). The chickens were then fed with unmedicated food up to day 7 after hatch. Fresh water was supplied ad libitum.

On day 8 after hatch, the four groups were fed as follows (1 ppm=1 mg drug/kg feed):

Group #1: feed containing JA 39 (100 ppm);

Group #2: feed containing JA 42 (100 ppm);

Group #3: feed containing Coxistac (60 ppm), a known anticoccidial agent (see U.S. Pat. No. 3,857,948);

Group #4: feed containing no drug (control group).

The chickens were fed as above on day 8 and 9 after hatch. On day 10 after hatch, each chicken was infected orally by 6 000–7 000 oocysts containing a mixture of 5 mature sporulated strains, namely *Eimeria acervulina, E. maxima, E. necatrix, E. tenella* and *E. brunetti*. The groups #1–3 received drug as above from day 10 to 21 after hatch.

From day 14 to 21 after hatch, fresh fecal droplets were collected and examined daily. The average number of oocysts/g faeces was then calculated in accordance with the so-called Mc-Master technique (Soulsby, E. J., *Helminths, Arthropods & Protozoa of domesticated animals*, p. 789, 6$^{th}$ Ed., Williams & Wilkins Co. Baltimore (USA), Tindall & Cassell Ltd., London, 1968). The final weight of and mean total amount of feed consumed by each bird were also examined, and the results are summarized in Table 8 hereinbelow.

TABLE 8

Anticoccidial effect of JA 39 and JA 42 on chicken

| Group (drug) | Average number of *Eimeria* spp. oocysts/g faeces | | | | | | | Mean body weight (g) | Mean amount of feed consumed (g) |
| --- | --- | --- | --- | --- | --- | --- | --- | --- | --- |
| | Day after hatch | | | | | | | | |
| | 14 | 15 | 16 | 17 | 18 | 19 | 21 | Total | | |
| #1 (JA 39) | 0.0 | 4000 | 5000 | 3000 | 0.0 | 0.0 | 0.0 | 12000 | 68.2 | 81 |
| #2 (JA 42) | 0.0 | 4000 | 6000 | 3000 | 0.0 | 0.0 | 0.0 | 13000 | 73.7 | 91 |
| #3 (Coxistac) | 0.0 | 3000 | 4000 | 7000 | 2000 | 2000 | 0.0 | 18000 | 62.0 | 120 |
| #4 (no drug) | 0.0 | 15000 | 24000 | $1.3 \times 10^6$ | 174000 | 0.0 | 0.0 | $1.4 \times 10^6$ | 57.3 | 120 |

As is evident from Table 8 above, the compounds JA 39 and JA 42 have excellent anticoccidial effect. This is also manifested in the higher mean body weight and lower amount of feed consumed as compared to both the Coxistac and the non-treated group.

Moreover, the prophylactic anticoccidial effect of JA 12, JA 39 and JA 42 was also evaluated in chickens of Arbor Aker breed. These trials were conducted by using basically the same test protocol as that used for the chickens of Habbared X breed, albeit with the following modifications:

i) On day 3 after hatch, the tested groups of chickens received feed containing 100 ppm of JA 12, JA 39, JA 42 or Coxistac (60 ppm);

ii) On day 7 after hatch, the chickens were infected orally by oocysts containing a mixture of 8 mature sporulated strains, namely E. mitis, E. hagani, E. praecox, E. acervulina, E. maxima, E. necatrix, E. tenella and E. brunetti.

For JA 39 and JA 42, the results were essentially the same as those reported for the trials with the chickens of Habbared X breed (vide supra), whereas the antiparasitic efficacy of JA 12 was very similar to that of JA 39.

In yet another evaluation of the prophylactic anticoccidial effect of the present compounds, additional trials on chickens of Habbared X breed were performed. The same test protocol as the one previously employed for this breed of chickens was used, albeit with the following following modifications:

i) On day 8 after hatch, the chickens received feed containing B700 (100 ppm), JA 3 (200 ppm) or Coxistac (100 ppm);

ii) On day 11 after hatch, the chickens were infected orally by oocysts containing a mixture of 8 mature sporulated strains, namely E. mitis, E. hagani, E. praecox, E. acervulina, E. maxima, E. necatrix, E. tenella and E. brunetti.

The results of this evaluation were slightly unexpected.

Both B700 and JA 3 displayed a significant anticoccidial activity, albeit the total number of oocysts during the treatment was higher than for the group treated with Coxistac. However, despite the said higher number of oocysts, the chickens treated with B700 or JA 3 experienced an approximately 10% increased body weight gain as compared to the Coxistac treated group. Moreover, a similar or even lowered (up to about 10%) feed consumption was observed in the chickens treated with B700 or JA 3. In short, the net effect of the treatment with B700 or JA 3 was clearly beneficial to the chickens.

Antiparasitic Testing Against Trypanosoma:

The antitrypanosomal activity of the present compounds was evaluated in vivo on 40 white albino rats. The rats were divided into 4 groups of 10 rats each. The rats were then inoculated intraperitoneally with $10^3$ organisms of T. evansi (isolated from blood of naturally infected camels) in accordance with known methodology (see Kolmer, J. A., J. Infect. Dis., 17:78–95 (1915)). The progress of the infection was monitored with the aid of standard Giemsa procedure (see Cruickshank, R., Handbook of Bacteriology, E and S Livingstone Ltd., Edinborough and London, 1961), whereby peripheral blood samples from the rats were examined under microscope. The number of Trypanosoma organisms in every blood sample was calculated and classified as follows (the numbers below are given for fields examined on a microscope slide):

+++=>10 organisms

++=5–10 organisms

+=1–4 organisms

0=no organisms detected

On day 1 post infection, each group of rats was subcutaneously injected with a single dose of tested compound in an amount of 50.0 mg/kg body weight. The following drugs were administered:

Group #1: JA 68

Group #2: JA 74

Group #3: JA 110

Group #4: saline solution (control group)

The results of these trials are depicted in Table 9 below:

TABLE 9

Antitrypanosomal effect of JA 68, JA 74 and JA 110 on white rat

| Tested animals | | Number of T. evansi per examined field at different days post infection | | | | | | |
|---|---|---|---|---|---|---|---|---|
| | | 1 | 3 | 5 | 7 | 9 | 11 | 13 |
| Group #1 (JA 68) | Mouse #1 | + | 0 | 0 | 0 | 0 | 0 | 0 |
| | 2 | + | ++ | ++ | 0 | 0 | 0 | 0 |
| | 3 | + | ++ | 0 | +++ | 0 | 0 | 0 |
| | 4 | + | ++ | ++ | 0 | dead | dead | dead |
| | 5 | + | ++ | 0 | 0 | 0 | 0 | 0 |
| | 6 | + | ++ | 0 | 0 | 0 | 0 | 0 |
| | 7 | + | ++ | 0 | 0 | 0 | 0 | 0 |
| | 8 | + | ++ | 0 | 0 | 0 | 0 | 0 |
| | 9 | + | ++ | 0 | 0 | 0 | 0 | 0 |
| | 10 | + | ++ | 0 | 0 | 0 | 0 | 0 |
| Group #2 (JA 74) | Mouse #1 | + | ++ | +++ | dead | dead | dead | dead |
| | 2 | + | ++ | 0 | 0 | 0 | 0 | 0 |
| | 3 | + | ++ | ++ | 0 | 0 | 0 | 0 |
| | 4 | + | +++ | ++ | 0 | 0 | 0 | 0 |
| | 5 | + | ++ | 0 | 0 | 0 | 0 | 0 |
| | 6 | + | ++ | 0 | 0 | 0 | 0 | 0 |
| | 7 | + | ++ | 0 | 0 | 0 | 0 | 0 |
| | 8 | + | ++ | 0 | 0 | 0 | 0 | 0 |
| | 9 | + | ++ | 0 | 0 | 0 | 0 | 0 |
| | 10 | + | ++ | + | 0 | 0 | 0 | 0 |
| Group #3 (JA 110) | Mouse #1 | + | +++ | ++ | ++ | + | + | 0 |
| | 2 | + | ++ | ++ | ++ | 0 | 0 | 0 |
| | 3 | + | ++ | ++ | ++ | 0 | 0 | 0 |
| | 4 | + | +++ | ++ | ++ | 0 | 0 | 0 |
| | 5 | + | ++ | ++ | ++ | 0 | 0 | 0 |
| | 6 | + | ++ | ++ | ++ | 0 | 0 | 0 |
| | 7 | + | ++ | ++ | ++ | 0 | 0 | 0 |
| | 8 | + | ++ | ++ | ++ | 0 | 0 | 0 |
| | 9 | + | ++ | ++ | ++ | 0 | 0 | 0 |
| | 10 | + | ++ | ++ | ++ | 0 | 0 | 0 |
| Group #4 (control) | Mouse #1 | + | ++ | ++ | +++ | +++ | dead | All animals dead |
| | 2 | ++ | ++ | +++ | +++ | dead | dead | |
| | 3 | + | +++ | +++ | +++ | +++ | +++ | |
| | 4 | + | ++ | ++ | +++ | +++ | dead | |
| | 5 | + | +++ | ++ | +++ | +++ | +++ | |
| | 6 | + | ++ | ++ | +++ | +++ | +++ | |
| | 7 | + | ++ | ++ | +++ | +++ | +++ | |
| | 8 | + | ++ | ++ | +++ | dead | dead | |
| | 9 | + | ++ | ++ | +++ | +++ | +++ | |
| | 10 | + | ++ | ++ | +++ | +++ | +++ | |

As supported by the results obtained (vide supra), the tested compounds are all highly suitable for treatment of Trypanosoma infection as well.

In summary, it should be clear from the present disclosure that the compounds according to the present invention are versatile new agents for antibacterial and/or antiparasitic treatment.

What is claimed is:

1. A compound having the formula (I):

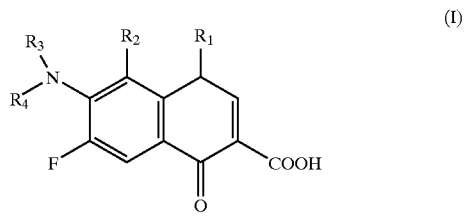

wherein $R_1$ is selected from the group consisting of a cyclopropyl group and an ethyl group;

$R_2$ is selected from the group consisting of H and F;

$R_3$ is selected from the group consisting of a 4-carboxycyclohexyl group, a 4-pyridinylmethyl group, 4-carboxybenzyl group, a 4-carboxyphenyl group, a [(trifluoromethyl)sulfonyl)]aminopropyl group, 2,2-dimethyl-3-[(trifluoromethyl)sulfony] aminopropyl group, a 2-[(trifluoromethyl)sulfonyl] aminoethyl group, a 5-bromo-2-pyrldinyl group, a tetrahydro-2-furanylmethyl group, a 2-(1-pyrrolidinyl) ethyl group, a 2-naphtylsulfonyl group, a 2-(4-pyridinyl)ethyl group, and a 2-(2-pyridinyl)ethyl group;

$R_4$ is selected from the group consisting of a (tifluoromethyl)sulfonyl group, a 2-thiophenylcarbonyl group, an acetoacetyl group, a 4-fluorophenylsulfonyl group, a 4-nitrophenyl group, and a tetrahydro-2-furanylmethyl group; or $R_3$ and $R_4$, together with the nitrogen to which they are attached, form a piperazinyl group substituted with a methyl group, a (4-nitrophenyl)sulfonyl group, an anilinocarbothioyl group, a 2-naphtylsulfonyl group, a (2,4,6-triisopropyl-phenyl)sulfonyl group, a (4-nitroanilino)carbothioyl group, a (4-fluoroanilino) carbothioyl group, a (6-chloro-2-pyrazinyl)-4-fluoroanilino carbthioyl group, a mesitylsulfonyl group, a benzylsulfonyl group, a (5-chloro-2-thienyl) sulfonyl group, a (4-nitroanilino)carbonyl group, a (2-iodoanilino)carbothioyl group, a (4-cyanoanilino) carbothioyl group, a (4-chlorobenzothioyl) group, a (2,4-dichloroanilino)carbothionyl group, a (2-chloro-4-nitroanilino)carbothioyl group, a 6-chloro-2-pyridinyl group, a (6-chloro-2-pyridinyl)-4-fluoroanilino) carbothioyl group, a 6-chloro-2-pyrazinyl group, and a (trifluoromethyl)sulfonyl group; or $R_3$ and $R_4$, together with the nitrogen to which they are attached, form a piperidinyl group substituted with a a 4-{[anilinocarbothioyl)amino]methyl} group.

2. A compound according to claim 1, having the formula (II)

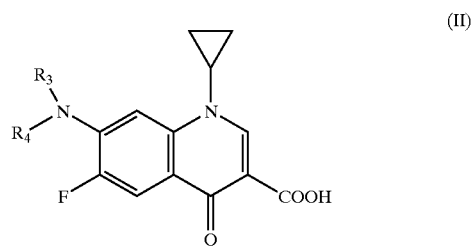

wherein $R_3$ is selected from the group consisting of a 4-carboxycyclohexyl group, a 4-pyridinylmethyl group, a 4-carboxybenzyl group, a 4-carboxyphenyl group, a [(trifluoromethyl)sulfonyl)]aminopropyl group, 2,2-dimethyl-3-[(trifluoromethyl)sulfonyl] aminopropyl group, a 2-[(trifluoromethyl)sulfonyl] aminoethyl group, a 5-bromo-2-pyridinyl group, a tetrahydro-2-furanylmethyl group, a 2-(1-pyrrolidinyl) ethyl group, a 2-naphtylsulfonyl group, a 2-(4-pyridinyl)ethyl group, a 2-(2-pyridinyl)ethyl group; and $R_4$ is selected from the group consisting of a (trifluoromethyl)sulfonyl group, a 2-thiophenylcarbonyl group, an acetoacetyl group, a 4-fluorophenylsulfonyl group, a 4-nitrophenyl group, a tetrahydro-2-furanylmethyl group.

3. A pharmaceutical composition comprising a compound according to claim 1 as active ingredient in association with a pharmaceutically acceptable adjuvant, diluent or carrier.

4. An animal feed, feed concentrate or drinking water comprising a compound according to claim 1.

5. A method for treatment of coccidiosis, wherein said method comprises administering to an animal of a therapeutically effective amount of a compound according to claim 1.

6. A pharmaceutical composition comprising a compound according to claim 2 as active ingredient in association with a pharmaceutically acceptable adjuvant, diluent or carrier.

7. An animal feed, feed concentrate or drinking water comprising a compound according to claim 2.

8. A method for treatment of coccidiosis, wherein said method comprises administering to an animal of a therapeutically effective amount of a compound according to claim 2.

9. A method according to claim 10, wherein said parasitic disorder is caused by *Trypanosoma*.

* * * * *